United States Patent [19]

Matsutani et al.

[11] Patent Number: 4,840,953
[45] Date of Patent: Jun. 20, 1989

[54] 9-(SUBSTITUTED THIO)-4H-PYRIDO[1,2,-A]PYRIMIDIN-4-ONE DERIVATIVES

[75] Inventors: Shigeru Matsutani; Yukio Mizushima; Masami Doteuchi; Yasunobu Ishihara, all of Osaka, Japan

[73] Assignee: Shionogi & Co., Ltd., Osaka, Japan

[21] Appl. No.: 206,665

[22] Filed: Jun. 15, 1988

Related U.S. Application Data

[63] Continuation of Ser. No. 911,359, Sep. 25, 1986, abandoned.

[30] Foreign Application Priority Data

Sep. 25, 1985 [JP] Japan .................................. 60-213181
Jan. 21, 1986 [JP] Japan .................................. 61-11591
Jul. 30, 1986 [JP] Japan .................................. 61-181159

[51] Int. Cl.$^4$ .................. C07D 471/04; A61K 31/505
[52] U.S. Cl. .................................... 514/258; 544/282;
546/283; 546/292; 546/297; 546/314; 546/315;
546/346; 548/248; 548/253; 549/71; 549/274;
549/483; 560/355; 560/358; 570/182; 260/544
R; 260/544 D

[58] Field of Search .......................... 544/282; 514/258

[56] References Cited

U.S. PATENT DOCUMENTS 3,960,847  6/1976  Yale ..................................... 544/282
4,022,897  5/1977  Yale ..................................... 544/282
4,122,274 10/1978  Juby ..................................... 544/282
4,209,620  6/1980  Juby ..................................... 544/252
4,457,932  7/1984  Juby ..................................... 514/258

FOREIGN PATENT DOCUMENTS 1492573  11/1977  United Kingdom ................ 544/282

Primary Examiner—Donald G. Daus
Assistant Examiner—E. Bernhardt
Attorney, Agent, or Firm—Birch, Stewart, Kolasch & Birch

[57]  ABSTRACT 9-(Substituted thio)-4H-pyrido[1,2-a]pyrimidin-4-one derivatives of the formula:

$$(O)_n-S-R \quad \quad (I)$$

(wherein n is 0 or 1, R is —COR$^1$, —CONR$^4$R$^5$ or —CH$_2$R$^6$, R$^1$ is C$_1$–C$_5$ alkyl, C$_3$–C$_7$ cycloalkyl, allythio, styryl, phenoxymethyl, thienylmethyl, C$_6$–C$_{10}$ aryl optionally substituted, benzyl optionally substituted or 5- or 6-membered heterocyclic group optionally substituted, R$^2$ and R$^3$ each is hydrogen, C$_1$–C$_5$ alkyl, carboxy, C$_2$–C$_5$ alkoxycarbonyl or benzyloxycarbonyl optionally substituted, R$^4$ and R$^5$ each is hydrogen, C$_1$–C$_5$ alkyl, C$_3$–C$_7$ cycloalkyl or phenyl optionally substituted, and R$^8$ is pyridyl or phenyl optionally substituted) being useful as antiulcer agents are provided through several routes.

6 Claims, No Drawings

9-(SUBSTITUTED THIO)-4H-PYRIDO[1,2,-A]PYRIMIDIN-4-ONE DERIVATIVES

This application is a continuation of copending application Ser. No. 911,359, filed on Sept. 25, 1986, now abandoned.

The present invention relates to 9-(substituted thio)-4H-pyrido[1,2-a]pyrimidin-4-one derivatives. More particularly, present invention is directed to 9-(substituted thio)-4H-pyrido[1,2-a]pyrimidin-4-one derivatives which have been found to be particularly effective in the treatment of peptic ulcers, to the preparation, and use thereof and, to pharmaceutical formulations containing the compounds.

U.S. Pat. No. 4,022,897 discloses 2-alkyl-9-(substituted oxy)-4H-pyrido[1,2-a]pyrimidin-4-one as a central nervous system stimulant, U.S. Pat. Nos. 4,122,274 and 4,209,620 describe 3-(1H-tetrazol-5-yl)-4H-pyrido[1,2-a]pyrimidin-4-ones as antiallergic agents, and U.S. Pat. No. 4,457,932 disclosed the use of said 3-(1H-tetrazol-5-yl)-4H-pyrido[1,2-a]-pyrimidin-4-ones as antiulcer agents.

The 9-(substituted thio)-4H-pyrido[1,2-a]pyrimidin-4-one derivatives of the present invention are those having a substituted thio group without 1H-tetrazol-5-yl and are therefore quite different from the compounds disclosed in the above references.

According to the present invention there is provided a 9(substituted thio)-4H-pyrido[1,2-a]pyrimidin-4-one derivative of the formula:

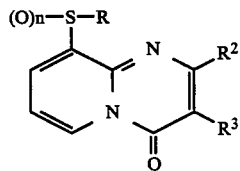

(I)

(wherein
n is 0 or 1,
R is —$COR^1$,

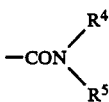

or —$CH_2R^6$, $R^1$ is $C_1$-$C_5$ alkyl, $C_3$-$C_7$ cycloalkyl, allylthio, styryl, phenoxymethyl, thienylmethyl, $C_6$-$C_{10}$ aryl optionally substituted by one or more members selected from the group consisting of $C_1$-$C_3$ alkyl, $C_3$-$C_6$ cycloalkyl, $C_1$-$C_3$ alkoxy, phenyl-$C_1$-$C_3$ alkoxy, halogen, nitro, $C_1$-$C_3$alkanesulfonyl, $C_2$-$C_5$ alkoxycarbonyl, cyano, acetoxy, acetyl, tetrazolyl, trifluoromethyl and sulfamoyl, benzyl optionally substituted by one or more members selected from the group consisting of $C_1$-$C_3$ alkyl, $C_1$-$C_3$ alkoxy, halogen and nitro, or 5- or 6- membered heterocyclic group optionally substituted by one or more members selected from the group consisting of $C_1$-$C_3$ alkyl, $C_1$-$C_3$ alkoxy and $C_3$-$C_6$ cycloalkyl, $R^2$ and $R^3$ each is hydrogen, $C_1$-$C_5$ alkyl, carboxy, $C_2$-$C_5$alkoxycarbonyl or benzyloxycarbonyl optionally substituted by one or more members selected from the group consisting of $C_1$-$C_3$ alkyl, $C_1$-$C_3$ alkoxy and halogen, $R^4$ and $R^5$ each is hydrogen, $C_1$-$C_5$ alkyl, $C_3$-$C_7$ cycloalkyl, or phenyl optionally substituted by one or more members selected from the group consisting of halogen, $C_1$-$C_3$ alkyl, $C_1$-$C_3$ alkoxy, $C_2$-$C_5$ alkoxycarbonyl, nitro and trifluoromethyl, and $R^6$ is pyridyl or phenyl optionally substituted by one or more members selected from the group consisting of halogen, $C_1$-$C_3$ alkyl and $C_1$-$C_3$ alkoxy.)
or its salt.

The compounds of the present invention has an excellent antiulcer activity with no undersirable action to human beings. Accordingly, the present invention also provides an antiulcer formulation comprising as an active ingredient 0.1 to 95% by weight of a compound of the formula (I) associated with at least one carrier, diluent or excipient therefor.

The present invention also provides a method of treating a patient suffering from peptic ulcer which comprises administering a pharmacologically effective amount of a compound of the formula (I) to the patient.

The present invention further provides a process for preparing a compound of the formula (I) which comprises (A) reacting a compound of the formula:

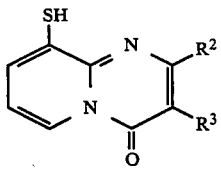

(II)

with a compound of the formula:

 $R^4$—NCO (III)

to give a compound of the formula:

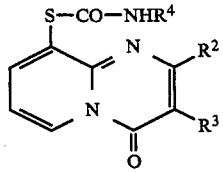

(Ia)

(B) reacting the compound of the formula (II) with N,N'-carbonyldiimidazole to give a compound of the formula:

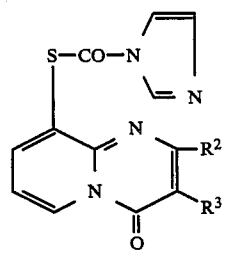

(IV)

and reacting the compound of the formula (IV) with a compound of the formula:

 $R^4NHR^5$ (V)

to give a compound of the formula:

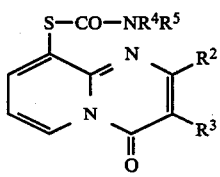
(Ib)

(C) reacting the compound of the formula (II) with a compound of the formula:

Hal—CH₂—R⁶    (VI)

to give a compound of the formula:

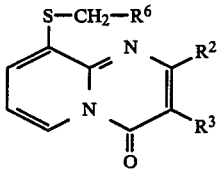
(Ic)

and eventually oxidizing the product (Ic) the 9-(substituted sylfinyl)-4H-pyrido[1,2-a]pyrimidin-4-one (Id) of the formula:

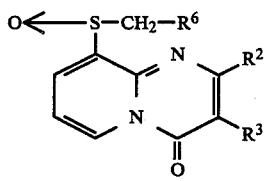
(Id)

or (D) reacting the compound of the formula (II) with a compound of the formula:

R¹COX    (VII)

to give a compound of the formula:

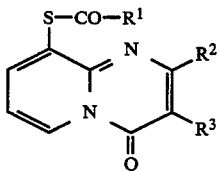
(Ie)

(wherein X is halogen, hydxoxy or reactive ester group of hydroxy; R¹, R², R³, R⁴ and R⁵ are as defined above).

The term "C₁-C₅ alkyl" herein employed refers to a straight or branched saturated aliphatic hydrocarbon radical such as methyl, ethyl, propyl, isopropyl, butyl, isobutyl, sec-butyl, tert-butyl, pentyl, isopentyl, neopentyl, tert-pentyl or 1-methylisobutyl. Among these, methyl and ethyl are preferred.

The term "C₃-C₇cycloalkyl" includes cyclopropyl, cyclobutyl, cyclopentyl, cyclohexyl and cycloheptyl.

The term "C₆-C₁₀ aryl" includes phenyl and naphthyl.

The term "C₁-C₃ alkoxy" refers to an alkoxy group containing C₁-C₃ alkyl moiety and includes methoxy, ethoxy and isopropoxy. The term "C₂-C₅ alkoxycarbonyl" refers to an alkoxycarbonyl group containing C₁-C₄alkyl moiety and includes methoxycarbonyl, ethoxycarbonyl, propoxycarbonyl and butoxycarbonyl.

The term "C₁-C₃ alkanesulfonyl" includes methanesulfonyl, ethanesulfonyl, propanesulfonyl and isopropanesulfonyl.

The term "halogen" includes fluorine, chlorine, bromine and iodine.

The term "5- or 6-membered heterocyclic group" refers to a 5- or 6-membered ring containing one or two hetero atoms such as nitrogen, oxygen or sulfur and includes furyl, thienyl, isoxazolyl, oxazolyl, thiazolyl and pyridyl moiety.

The reactive ester of hydroxy group includes an inorganic acid ester such as sulfate or phosphate and an organic acid ester such as methanesulfonate, toluenesulfonate, ethoxycarbonate and trifluoromethanesulfonate.

The process for preparing the compound (I) will be detailed below.

METHOD A

The compound (Ia) of the invention is prepared by reaction of the compound (II) with the compound (III). Thus, 9-mercapto-4H-pyrido[1,2-a]pyrimidine (II) and isocyanates (III) are allowed to react in the range of temperature from about 0° C. to about 80° C., preferably at room temperature (10° to 30° C.) for 1 to 10 hours.

The reaction is usually conducted in a solvent such as dichloromethane, 1,2-dichloroethane, chloroform, carbontetrachloride, cyclopentane, cyclohexane, n-hexane, benzene, ethyl acetate, acetonitrile, tetrahydrofuran, acetone, methyl ethyl ketone or the like.

The isocyanates (III) can be manufactured by reacting a corresponding amine with phosgene [Slocombe et al., J. Am. Chem. Soc., 72, 1888 (1950)] or with oxalyl chloride [Ulrich et al., J. Org. Chem., 34, 3200 (1969)].

METHOD B

The compound (Ib) is prepared by reacting the compound (II) with N,N'-carbonyldiimidazole to give the imidazolyl compound (IV) and then reacting the compound (IV) with the amine (V).

At first the carbonylation of the compound (II) is conducted in the range of temperature from about 0° C. to about 100° C., preferably around room temperature in an appropriate solvent such as dichloromethane, 1,2-dichloroethane, chloroform, carbon tetrachloride, benzene, tetrahydrofuran, acetonitrile, ethyl acetate or the like.

Secondly the imidazolyl compound (IV) thus obtained is allowed to react with the amine (V). This reaction is conducted in the range of temperature from room temperature to about 100° C. in a solvent as mentioned in the above step.

METHOD C

The compound (Ic) is prepared by reacting the compound (II) with the halide (VI). Thus the 9-mercapto-4H-pyrido[1,2-a]-pyrimidin-4-one (II) is allowed to react with the halide (VI) in the presence of a base in an appropriate solvent in the range of temperature from about 10° C. to about 100° C.

As the base, there are exemplified inorganic bases, for example, alkali or alkaline earth metal hydroxides such as sodium hydroxide, potassium hydroxide and calcium hydroxide; alkali carbonate such as sodium carbonate and potassium carbonate; organic bases such as triethylamine, N-methylpyrrolidine, N-ethylpiperidine, morpholine, pyridine, picoline and lutidine. Illustrative of the solvent are methanol, ethanol, isopropanol, acetone, methyl ethyl ketone, ether, tetrahydrofuran, dimethylformamide, dimethylacetamide and dimethyl sulfoxide.

Eventually the compound (Ic) above obtained is oxidized with a peroxide in the range of temperature from about −50° to about 10° C. The oxidation may be conducted in an appropriate solvent such as chloroform, dichloromethane, 1,2-dichloroethane, carbon tetrachloride, benzene or toluene. They may be suitably selected depending upon the qualities of the peroxide used. The peroxide includes a hydroperoxide such as hydrogen peroxide, ethyl hydroperoxide and tert-butyl hydroperoxide and a peracid such as peracetic acid, perbenzoic acid and 3-chloroperbenzoic acid. When the hydroperoxide is used, the reaction can be accelerated by adding sulfuric acid, hydrochloric acid, p-toluenesulfonic acid, methanesulfonic acid or aluminum chloride.

METHOD D

The compound (Ie) is prepared by reacting the compound (II) with the compound (VII). Thus 9-mercapto-4H-pyrido[1,2-a]-pyrimidin-4-one (II) is allowed to react with the acylating reagent (VII).

The acylation is conducted in a conventional manner in the range of temperature from about 0° C. to about 80° C., preferably around room temperature in the presence of a base in an appropriate solvent. Examples of the solvent are dichloromethane, 1,2-dichloroethane, chloroform, cyclohexane, n-hexane, benzene, acetone, acetonitrile, tetrahydrofuran, and the like. The base as exemplified in Method C may be used in this Method D.

Alternatively the acylation with the carboxylic acid (VII) may be attained by conducting the reaction in the presence of a dehydrating agent such DCC or the like in a solvent. Further the acylation with the carboxylic acid (VII) and lower alkyl chlorocarbonate-triethylamine can be performed in a solvent at 0° C. to 100° C. These reactions may be conducted in a conventional manner.

Moreover the compound (Ie) may be prepared by reacting the compound (Ib) with the acid halide (VII) in the presence of Lewis acid such as zinc iodide, zinc chloride, triethyl borate or aluminum chloride. This reaction is conducted in an appropriate solvent such as 1,2-dichloroethane, methylene chloride or toluene by heating around the boiling point of the solvent used.

PREPARATION OF THE STARTING COMPOUND (II)

The starting compound (II) can be prepared as shown in the following synthetic processes.

Introduction of a thiol group can be carried out by any one of the synthetic methods described in Saul Patail, "The Chemistry of the Thiol Group", An Interscience Publication, p. 163–269 (1974). The conversion of a hydroxy group to a thiol group will be illustratively shown below.

SYNTHETIC PROCESS (1) OF STARTING MATERIALS

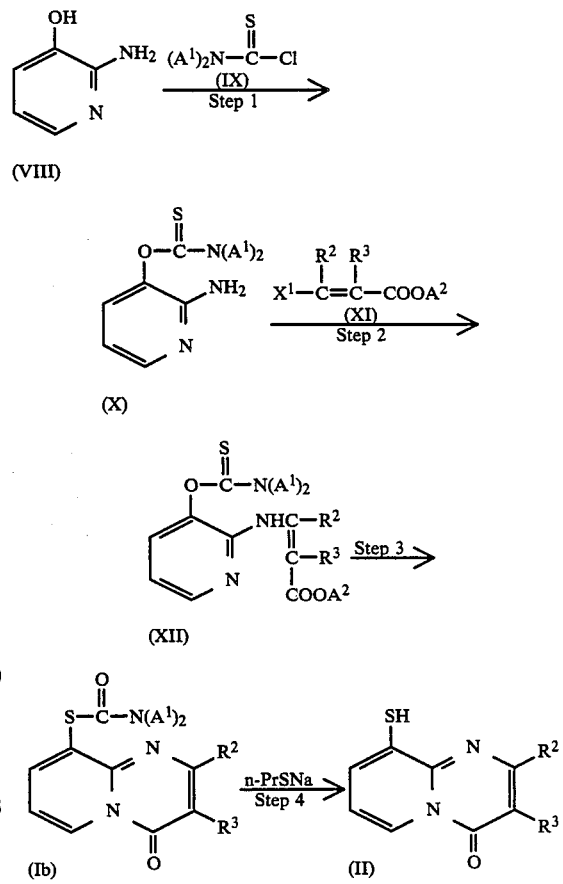

(Wherein $A^1$ and $A^2$ each is lower alkyl, $X^1$ is a leaving group such as halogen, amino, lower alkoxy, lower alkylthio, mesyloxy or tosyloxy, and $R^2$ and $R^3$ are as defined above).

STEP 1

The starting 2-amino-3-hydroxypyridine (VIII) is allowed to react with thiocarbamoyl chloride (IX) in the presence of a base, affording the compound (X). The reaction is conducted at 0° to 80° C., preferably room temperature in a solvent such as acetone, methyl ethyl ketone, ethyl acetate, tetrahydrofuran, toluene, ether, dioxane, dimethyl sulfoxide, dimethylformamide or dimethylacetamide. Examples of the base are those as described in Method C, Step 1.

STEP 2

The 2-amino-3-thiocarbamoyloxypyridine (X) is allowed to react with the ester (XI) in the range of temperature from room temperature to about 150° C., preferably about 100°–120° C., affording the enamine (XII). The reaction is conducted in the presence or absence of a solvent. If any solvent is used, the solvent includes aprotic solvents such as ether, tetrahydrofuran, dioxane, dimethylformamide, benzene and toluene. If necessary, the bases as illustrated in Method C may be added for accelerating the reaction.

The reagent (XI) can be manufactured by the methods disclosed in R. M. Carlson et al., Tetrahedron Letters, 4819 (1973) and G. H. Posner et al., Chem. Commun. 907 (1973) or by the methods quoted therein.

STEP 3

Subjecting the enamine (XII) to this step, the compound (Ib) is prepared by the ring closure and concomitant O→S rearrangement. The reaction will terminate in several minutes by refluxing in a solvent such as toluene, xylene or a diphenyl ether having a boiling point more than 100° C., preferably more than 200° C.

STEP 4

The compound (Ib) is allowed to react with sodium n-propyl mercaptide, affording the compound (II). The reaction is conducted at 0° to 80° C., preferably 0° C. to room temperature in a solvent such as THF, dioxane, ethanol, toluene, dimethylformamide or dimethyl sulfoxide.

SYNTHETIC PROCESS (2) OF STARTING MATERIALS

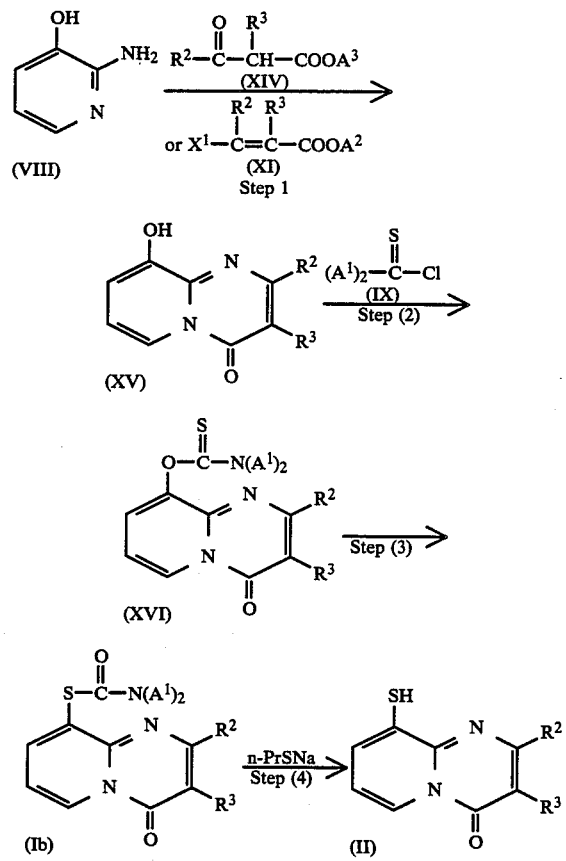

(wherein $A^1$, $A^3$, $R^2$, $R^3$ and $X^1$ are as defined above).

STEP 1

The 2-amino-3-hydroxypyridine (VIII) is allowed to react with the β-oxocarboxylic ester (XIV) in the presence of an acidic condensing agent, affording the compound (XV). The reaction is conducted in the range of temperature from 50° to 150° C., preferably 80° to 120° C. The acidic condensing agent includes polyphosphoric acid, acetic acid, propionic acid and the like. If necessary, any solvent such as water, methanol, ethanol, isopropanol, n-butanol or the like may be added.

The β-oxocarboxylic ester (XIV) can be manufactured by the method dislosed in C. R. Hauser et al., Organic Reactions, 1, 266 (1942).

Alternatively, the 9-hydroxy-4H-pyrido[1,2-a]pyrimidin-4-one (XV) can be prepared by reacting the 2-amino-3-hydroxypyridine (VIII) with the ester (XI). The reaction can be conducted as in Synthetic Process (1) Step 2.

STEP 2

The reaction is conducted as in Synthetic Process (1) Step 1.

STEP 3

The reaction is conducted at 100° to 170° C. in a solvent such as toluene, xylene, anisole, diethylene glycol or tetrachloroethane, as in Synthetic Process (1) Step 3.

STEP 4

The reaction is conducted as in Synthetic Process (1) Step 4.

The objective compound (I) of the present invention can be converted into its salts. Depending upon the kind of substituents and the like, it can be converted into alkaline metal salts (e.g. lithium salt, sodium salt, potassium salt, etc.) or alkaline earth metal salts (e.g. calcium salt, magnesium salt, etc.), Further the objective compound (I) can be eventually converted into its acid addition salts. The acids usable in this case include inorganic acids such as hydrochloric acid, hydrobromic acid and phosphoric acid, and organic acids such as acetic acid, oxalic acid, maleic acid, fumaric acid, citric acid, malic acid, adipic acid and succinic acid.

The objective compound (I) of the present invention and/or its salts can be administered orally or parenterally to humans or animals. For example, the compound (I) can be administered orally in the form of tablets, granules, powders, capsules, or liquid and parenterally in the form of injection or suppository.

These preparations can be prepared in a conventional manner by using diluents, binders, disintegrators, lubricants, stailizers, suspending agents, dispersants, solubilizers, antiseptics and the like.

The diluents include illustratively lactose, sucrose, starch, cellulose, sorbit, etc.; the binders include gum arabic, gelatin, polyvinylpyrrolidone, etc.; the lubricants include magnesium stearate, talc, silica gel, etc.

When the compound (I) of the present invention is used for the treatment of peptic ulcer in human adults, about 1-100 mg/Kg of the compound (I) may be administered orally or parenterally once or in several divisions per day.

The present invention will be explained in more detail by the following Examples, Referential Examples, and Formulation.

The abbreviations used in Examples, Referential Examples, and Tables each has the following meanings.

Me=methyl; Et=ethyl; n-Pr=n-propyl; t-Bu=t-butyl; $CH_2Cl_2$=dichloromethane; $CHCl_3$=chloroform; AcOEt=ethyl acetate; THF=tetrahydrofuran; $K_2CO_3$=potassium carbonate DMF=dimethylformamide; NaH=sodium hydride (60% oily suspension); m-CPBA=3-chloroperbenzoic acid; (d)=decomposing point.

EXAMPLE 1

Preparation of
3-ethoxycarbonyl-9-(4-methylphenylcarbamoylthio)-
4H-pyrido[1,2-a]pyrimidin-4-one Ia1.

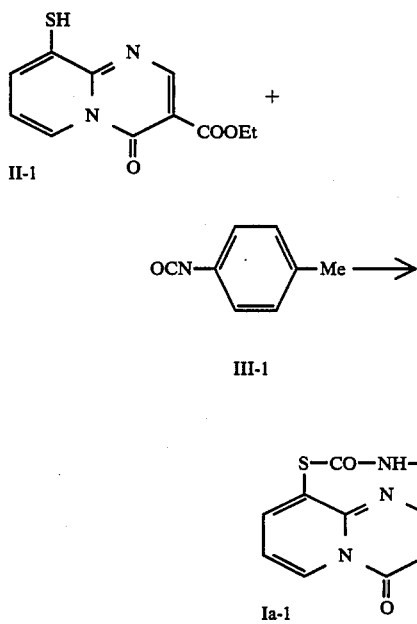

To a suspension of 0.4 g of 3-ethoxycarbonyl-9-mercapto-4H-pyrido[1,2-a]pyrimidin-4-one II-1 in 10 ml of dry CH$_2$Cl$_2$ is added 0.35 g of 4-methylphenyl isocyanate III-1, and the resultant mixture is stirred at room temperature for 4 hours. At this time the reaction mixture is crystallized again after it is once dissolved.

Then the product is filtered, washed with AcOEt and recrystallized from AcOEt to give 0.441 g of the titled compound Ia1.

Yield: 72%, m.p.: 170°–172° C.,

Anal. Calcd. for C$_{19}$H$_{17}$O$_4$N$_3$S: C,59.52; H,4.47; N,10.96; S,8.36:(%), Found: C,59.52; H,4.45; N,10.84; S,8.47:(%),

EXAMPLE 2–19

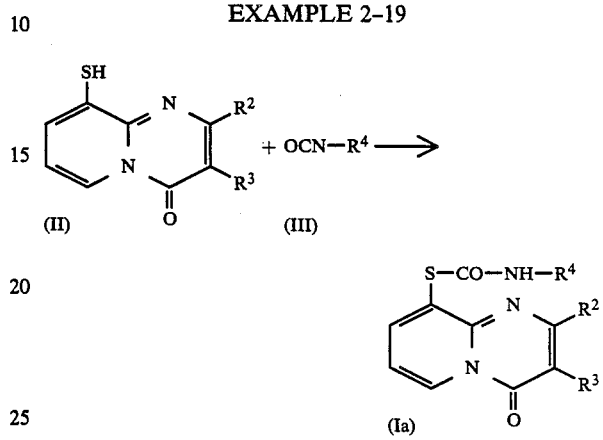

To a suspension of 9-mercapto-4H-pyrido[1,2-a]pyrimidin-4-one (II) in an appropriate solvent is added the isocyanate (III), and the resultant mixture is stirred at room temperature for about 1–5 hours. The crystal precipitated is filtered, washed with AcOEt and recrystallized from AcOEt to give the objective compound (Ia).

Table 1 shows the reaction conditions for preparing the compound (Ia) (i.e. structure and amount of the reactants, solvents, the reaction time, etc.), and the structure of the product (Ia) and their physical constants (i.e. melting point and elementary analysis).

TABLE 1

$$\underset{(II)}{\begin{array}{c}\text{SH}\\ \diagup\diagdown\\ \text{N}\end{array}} + \underset{(III)}{\text{OCN}-R^4} \longrightarrow \underset{(Ia)}{\begin{array}{c}\text{S}-\text{CO}-\text{NH}-R^4\\ \diagup\diagdown\\ \text{N}\end{array}}$$

| Ex. No. | R² | R³ | R⁴ | Supplied Amount (g) Compd. (II) | Isocyanate (III) | Solvent (ml) | Reaction Time (hr) | Compd. No. | Yield (%) | m.p. (°C.) | Molecular Formula | Elementary Analysis (%) up: Found down: Calcd. C | H | N | S | Cl | F |
|---|---|---|---|---|---|---|---|---|---|---|---|---|---|---|---|---|---|
| 2 | H | COOEt | n-Pr | 0.6 | 0.23 | CH₂Cl₂ (10) | 1 | Ia-2 | 37 | ~250 | C₁₅H₁₇O₄N₃S | 53.72 53.43 | 5.11 4.80 | 9.56 9.56 | 12.53 12.16 | | |
| 3 | H | COOEt | 4-Cl-C₆H₄ | 1.0 | 0.65 | CHCl₃ (20) | 1 | Ia-3 | 68.2 | 184~186 | C₁₈H₁₄O₄N₃SCl | 53.66 53.54 | 3.65 3.49 | 10.13 10.41 | 7.73 7.94 | 8.39 8.78 | |
| 4 | H | COOEt | C₆H₅ | 0.347 | 0.22 | CHCl₃ (10) | 1 | Ia-4 | 58.6 | 164~167 | C₁₈H₁₅O₄N₃S | 58.54 58.53 | 4.17 4.09 | 11.35 11.38 | 8.46 8.68 | | |
| 5 | H | COOEt | 4-F-C₆H₄ | 0.4 | 0.35 | CH₂Cl₂ (17) | 1 | Ia-5 | 80.0 | 168~171(d) | C₁₈H₁₄O₄N₃SF | 55.56 55.81 | 3.61 3.64 | 10.83 10.85 | 8.40 8.28 | | 5.09 4.90 |
| 6 | H | COOEt | 3-OMe-C₆H₄ | 0.5 | 0.4 | CH₂Cl₂ (20) | 3 | Ia-6 | 68 | 155~157(d) | C₁₉H₁₇O₅N₃S | 56.94 57.13 | 4.30 4.29 | 10.42 10.52 | 7.90 8.03 | | |
| 7 | H | COOEt | 4-OMe-C₆H₄ | 0.5 | 0.4 | CH₂Cl₂ (15) | 3 | Ia-7 | 70 | 162~164(d) | C₁₉H₁₇O₅N₃S | 56.90 57.13 | 4.29 4.29 | 10.53 10.52 | 8.04 8.03 | | |

TABLE 1-continued $$\underset{(II)}{\text{SH-pyridine-N=C(R}^2\text{)-C(R}^3\text{)=C(=O)-N}} + \text{OCN-R}^4 \longrightarrow \underset{(Ia)}{\text{S-CO-NH-R}^4\text{-pyridine}}$$

| Ex. No. | R² | R³ | R⁴ | Supplied Amount (g) Compd. (II) | Supplied Amount (g) Isocyanate (III) | Solvent (ml) | Reaction Time (hr) | Compd. No. | Yield (%) | m.p. (°C.) | Molecular Formula | Elementary Analysis (%) up: Found down: Calcd. C | H | N | S | Cl | F |
|---|---|---|---|---|---|---|---|---|---|---|---|---|---|---|---|---|---|
| 8 | H | COOEt | 2-OMe-C₆H₄ | 0.5 | 0.4 | CH₂Cl₂ (15) | 2 | Ia-8 | 84.5 | 265~267 | C₁₉H₁₇O₆N₃S | 57.32 57.13 | 4.40 4.29 | 10.32 10.52 | 7.97 8.03 | | |
| 9 | H | COOEt | 4-CF₃-C₆H₄ | 0.5 | 0.5 | CH₂Cl₂ (15) | 4 | Ia-6 | 75 | 185~188(d) | C₁₉H₁₄O₄N₃SF₃ | 52.19 52.17 | 3.35 3.23 | 9.54 9.61 | 7.51 7.33 | | 13.04 13.03 |
| 10 | Me | H | 4-Me-C₆H₄ | 0.4 | 0.4 | CH₂Cl₂ (12) | 2 | Ia-10 | 76.8 | 237~238 | C₁₇H₁₅O₂N₃S | 62.61 62.75 | 4.78 4.65 | 12.94 12.91 | 9.92 9.85 | | |
| 11 | Me | H | C₆H₅ | 0.5 | 0.4 | CH₂Cl₂ (10) | 3 | Ia-11 | 87 | 240~241 | C₁₆H₁₃O₂N₃S | 61.59 61.72 | 4.20 4.21 | 13.57 13.50 | 10.23 10.30 | | |
| 12 | Me | H | 4-Cl-C₆H₄ | 0.44 | 0.4 | CH₂Cl₂ (10) | 1 | Ia-12 | 65 | 240~241 | C₁₆H₁₂O₂N₃SCl | 55.44 55.57 | 3.67 3.45 | 12.39 12.15 | 9.12 9.27 | | |
| 13 | H | COOEt | 3-Me-C₆H₄ | 0.7 | 0.6 | CH₂Cl₂ (17) | 4 | Ia-13 | 88.9 | 161~165(d) | C₁₉H₁₇O₄N₃S | 59.46 59.52 | 4.60 4.47 | 10.94 10.96 | 8.44 8.37 | | |

TABLE 1-continued $$\underset{(II)}{\begin{array}{c}SH\\\diagdown\\N\end{array}} \underset{R^2}{\overset{R^3}{\diagdown}} \underset{O}{\overset{}{\diagup}} + OCN-R^4 \longrightarrow \underset{(Ia)}{\begin{array}{c}S-CO-NH-R^4\\\diagdown\\N\end{array}} \underset{R^2}{\overset{R^3}{\diagdown}} \underset{O}{\overset{}{\diagup}}$$

| Ex. No. | R² | R³ | R⁴ | Supplied Amount (g) Compd. (II) | Supplied Amount (g) Isocyanate (III) | Solvent (ml) | Reaction Time (hr) | Compd. No. | Yield (%) | m.p. (°C.) | Objective Compound (Ia) Molecular Formula | Elementary Analysis (%) up: Found down: Calcd. C | H | N | S | Cl | F |
|---|---|---|---|---|---|---|---|---|---|---|---|---|---|---|---|---|---|
| 14 | H | COOEt | 2-Me-C₆H₄ | 0.7 | 0.6 | CH₂Cl₂ (17) | 3 | Ia-14 | 83.9 | 153~156(d) | C₁₉H₁₇O₄N₃S | 59.62 59.52 | 4.45 4.47 | 10.97 10.96 | | | 0.04 8.36 |
| 15 | H | COOEt | 4-NO₂-C₆H₄ | 0.7 | 0.6 | CH₂Cl₂ (15) | 3 | Ia-15 | 95 | 214~216 | C₁₈H₁₄O₆N₄S | 52.30 52.17 | 3.37 3.41 | 13.52 13.52 | 7.76 7.74 | | |
| 16 | H | COOEt | Me | 0.7 | 0.3 | CH₂Cl₂ (15) | 3 | Ia-16 | 81.4 | 259~261 | C₁₃H₁₃O₄N₃S | 51.02 50.81 | 4.26 4.26 | 13.64 13.67 | 10.12 10.43 | | |
| 17 | H | COOEt | t-Bu | 0.7 | 0.4 | CH₂Cl₂ (17) | 3 | Ia-17 | 61.4 | 154~156 | C₁₆H₁₉O₄N₃S·½H₂O | 54.33 54.21 | 5.22 5.49 | 11.77 11.85 | | | |
| 18 | H | COOEt | cyclohexyl | 0.7 | 0.4 | CH₂Cl₂ (17) | 3 | Ia-18 | 60 | 149~151(d) | C₁₈H₂₁O₄N₃S | 57.33 57.59 | 5.53 5.64 | 11.19 11.19 | 8.38 8.54 | | |
| 19 | H | COOEt | 4-COOMe-C₆H₄ | 0.5 | 0.5 | CH₂Cl₂ (10) | 4 | Ia-19 | 61.2 | 174~175 | C₂₁H₁₉O₆N₃S | 57.09 57.14 | 4.34 4.34 | 9.56 9.52 | 7.05 7.26 | | |

EXAMPLE 20

Preparation of
3-ethoxycarbonyl-9-(N-ethyl-N-phenylcarbamoylthio)-
4H-pyrido[1,2-a]pyrimidin-4-one Ib-20

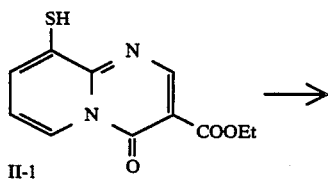

II-1

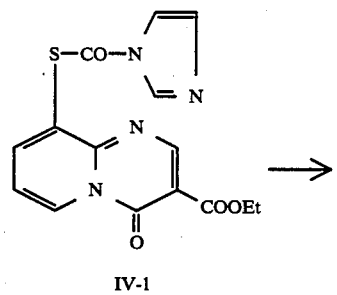

IV-1

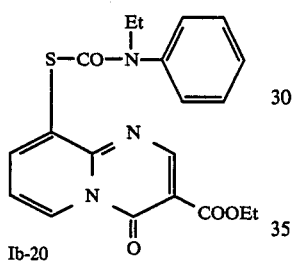

Ib-20

To a suspension of 0.413 g of 3ethoxycarbonyl-9-mercapto-4H-pyrido[1,2-a]pyrimidin-4-one II-1 in 10 ml of CH₂Cl₂ is added 0.3 g of N,N'-carbonyldiimidazole under stiring, and the resultant mixture is stirred for 1 hour. The reaction mixture is mixed with 0.2 g of N-ethylaniline V-1 and stirred for another 16 hours. After finishing the reaction, the solvent is evaporated in vacuo, and the residue is chromatographed on a column of silica gel to give 0.34 g of the titled compound Ib-20 as a viscous oily material.

NMR (CDCl₃) δ: 1.11 (3H, t, J=7Hz), 1.27 (3H, d, J=7Hz), 3.22 (2H, q, J=7Hz), 4.15 (2H, q, J=7Hz), 6.80–7.80 (8H, m), 7.96 (1H, s), mass spectrum, M+ (m/e): 397

EXAMPLE 21

(1) Preparation of
3-ethoxycarbonyl-9-benzylthio-4H-pyrido[1,2-a]pyrimidin-4-one Ic-21.

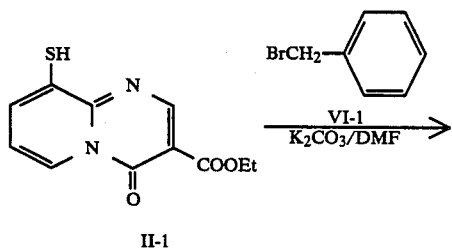

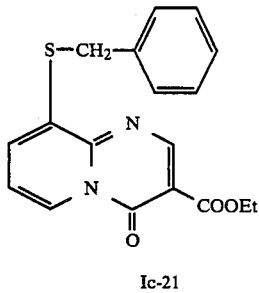

Ic-21

To a suspension of 0.3 g of 3-ethoxycarbonyl-9-mercapto-4H-pyrido[1,2-a]pyrimidin-4-one II-1 in 4 ml of anhydrous DMF are added 0.3 g of benzyl bromide VI-1 and 0.5 g of K₂CO₃, and the resultant mixture is stirred at room temperature for 5 hours. The reaction mixture is diluted with water. The crystal precipitated is filtered and dissolved in CHCl₃. The chloroform solution is dried over Na₂SO₄ and evaporated to give 0.389 g of the titled compound Ic-21.

Yield: 95.3%, m.p.: 173°–174° C. (recrystallized from AcOEt),

Anal. Calcd. for C₁₈H₁₆O₃N₂S: C, 63.51; H, 4.74; N, 8.23; S, 9.42(%),

Found: C, 63.48; H, 4.63; N, 8.17; S, 9.30(%).

(2) Preparation of
3-ethoxycarbonyl-9-benzylsulfinyl-4H-pyrido[1,2-a]pyrimidin-4-one Id-22.

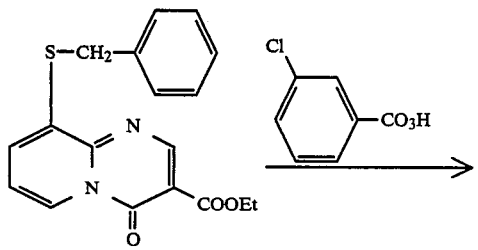

Id-22

A solution of 3-ethoxycarbonyl-9-benzylmercapto-4H-pyrido-[1,2-a]pyrimidin-4-one Ic-21 provided in said item (1) in 25 ml of CHCl₃ is cooled to 0° C., and 0.5 g of m-CPBA is added in the solid form under stirring. The mixture is stirred at the same temperature for 4 hours. The reaction mixture is washed with 5% aqueous solution of sodium thiosulfate, 5% aqueous solution of sodium hydrogencarbonate and water, successively. After the resulting mixture is dried over anhydrous sodium sulfate, its solvent is evaporated.

The residue (1 g) is purified by flash chromatography, eluting with AcOEt. The solid prepared from the eluate is recrystallized with AcOEt to give 0.6 g of the titled compound Id-22.

Yield: 81.9%,
m.p.: 175°–176° C.,
Anal. Calcd. for $C_{18}H_{16}O_4N_2S$ C, 60.66; H, 4.53; N, 7.86; S, 9.00(%),
Found: C, 60.72; H, 4.64; N, 7.75; S, 8.80(%).

EXAMPLE 22–23

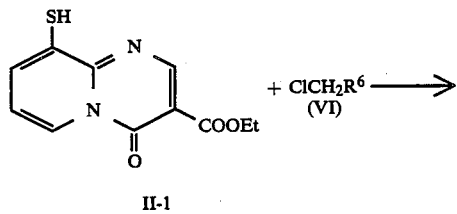

II-1

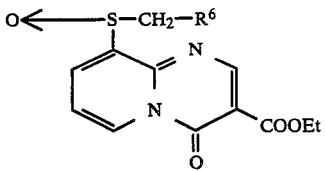

(Id)

(1) To a suspension of 3-ethoxycarbonyl-9-mercapto-4H-pyrido-[1,2-a]pyrimidin-4-one II-1 in anhydrous DMF are added the chloride (VI) and $K_2CO_3$, and the mixture is stirred at room temperature for several hours. The reaction mixture is diluted with water. The crystal precipitated is filtered and dissolved in $CHCl_3$. The resulting mixture is dried over anhydrous sodium sulfate. The solvent is evaporated from the mixture to give the compound (Ic).

Table 2 shows the reaction conditions for preparing the compound (Ic) (i.e. structure and amount of the reactants, solvents, the reaction time, etc.), and the structure of the product (Ic) and their physical constants (i.e. melting point and elementary analysis).

TABLE 2

| Ex. No. | $R^6$ | Compd. (II-1) | Compd. (VI) | $K_2CO_3$ | Amount of DMF (ml) | Reaction Time (hr) |
|---|---|---|---|---|---|---|
| 22(1) | 3-fluorophenyl | 0.25 | 0.16 | 0.5 | 3 | 2 |
| 23(1) | 2-pyridyl | 1.5 | 1.0* | 2.0 | 20 | 4 |

| | Objective Compound (Ic) | | | | Elementary Analysis (%) Up: Found Down: Calcd. | | | | |
|---|---|---|---|---|---|---|---|---|---|
| Ex. No. | Compd. No. | Yield (%) | m.p. (°C.) | Molecular Formula | C | H | N | S | F |
| 22(1) | Ic-23 | 98 | 168~169 | $C_{18}H_{16}O_3N_2SF$ | 60.23 | 4.30 | 7.76 | 9.09 | 5.55 |
| | | | | | 60.33 | 4.22 | 7.82 | 8.95 | 5.30 |
| 23(1) | Ic-25 | 58.6 | 158~159 | $C_{17}H_{15}O_3N_3S$ | 59.91 | 4.41 | 12.22 | 9.62 | |
| | | | | | 59.81 | 4.43 | 12.31 | 9.39 | |

*Amount as HCl salt

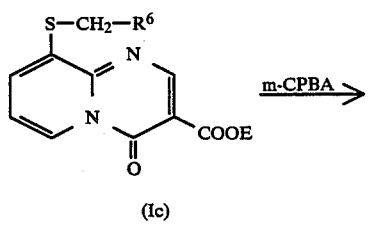

(Ic)

(2) To a solution of the compound (Ic) in $CHCl_3$, is added m-CPBA under cooling and stirring, and the resultant mixture is stirred at the same temperature for several hours. The reaction mixture is washed with 5% aqueous solution of sodium thiosulfate, 5% aqueous solution of sodium hydrogencarbonate and water, successively. After the resultant mixture is dried over anhydrous sodium sulfate, the solvent is evaporated. The residue is purified by flash chromatography eluting with AcOEt. The solid obtained from the eluate is recrystallized with AcOEt to give the compound (Id).

Table 3 shows the reaction conditions for preparing the compound (Id) (i.e. structure and amount of the reactants, solvents the reaction time, etc.), and the structure of the product (Id) and their physical constants (i.e. melting point and elementary analysis).

TABLE 3

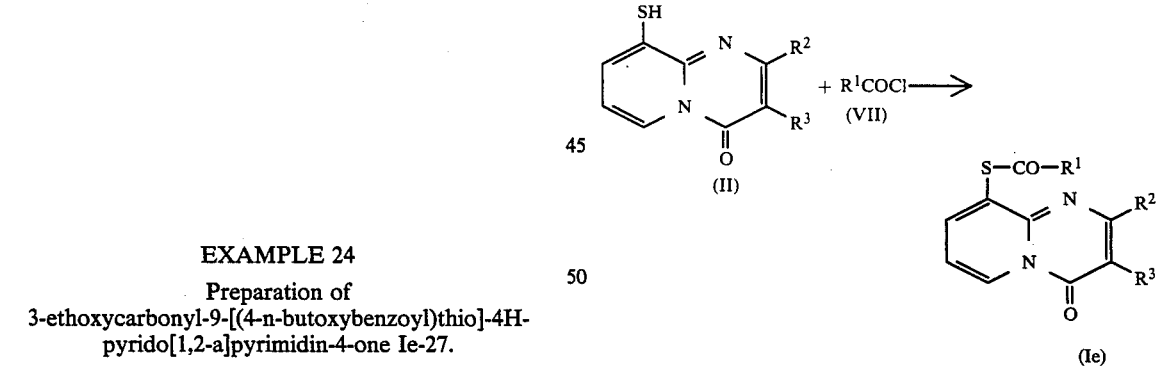

| Ex. No. | $R^6$ | Supplied Amount (g) Compd. (Ic) | m-CPBA | Amount of CHCl$_3$ (ml) | Reaction Temperature (°C.) | Reaction Time (hr) |
|---|---|---|---|---|---|---|
| 22-(2) | (4-F-phenyl) | 1.0 | 0.7 | 30 | −5∼+10 | 2 |
| 23-(2) | (pyridyl) | 0.7 | 0.5 | 25 | −5∼+5 | 2 |

| | | | Compound (Id) | | Elementary Analysis (%) up: Found Down: Calcd. | | | | |
|---|---|---|---|---|---|---|---|---|---|
| Ex. No. | Compd. No. | Yield (%) | m.p. (°C.) | Molecular Formula | C | H | N | S | F |
| 22-(2) | Id-24 | ∼100 | 171–172 | C$_{18}$H$_{15}$O$_4$N$_2$SF | 57.43 57.75 | 4.02 4.04 | 7.37 7.48 | 8.80 8.56 | 5.34 5.07 |
| 23-(2) | Id-26 | 74.3 | 183–185 | C$_{17}$H$_{15}$O$_3$S.½H$_2$O | 55.89 55.73 | 4.19 4.40 | 11.37 11.47 | 8.86 8.75 | |

EXAMPLE 24

Preparation of 3-ethoxycarbonyl-9-[(4-n-butoxybenzoyl)thio]-4H-pyrido[1,2-a]pyrimidin-4-one Ie-27.

To a mixture of 0.8 g of 3-ethoxycarbonyl-9-mercapto-4H-pyrido[1,2-a]pyrimidin-4-one II-1, 0.5 g of powdery potassium carbonate and 25 ml of acetone is added 0.7 g of 4-n-butoxybenzoyl chloride with stirring, and the resultant mixture is stirred at room temperature for 2 hours. The resultant precipitate is filtered and distributed in water-chloroform. The chloroform layer is washed with saturated brine, dried over sodium sulfate and concentrated. The residue (1.1 g) is chromatographed on a column of silica gel, eluting with ethyl acetate. Concentration of the eluate affords 0.7 g of the titled compound.

Yield: 51%,

Anal. Calcd. for C$_{22}$H$_{22}$O$_5$N$_2$S C, 61.96; H, 5.20; N, 6.57; S, 7.52(%), Found: C, 61.73; H, 5.22; N, 6.47; S, 7.65(%).

EXAMPLE 25–50

To a suspension or solution of 9-mercapto-4H-pyrido[1,2-a]pyrimidin-4-one (II) in an appropriate solvent are added an appropriate base and then an acid chloride (VII), and the resultant mixture is stirred at room temperature for about 1 to 5 hours. The reaction mixture is concentrated in vacuo to dryness, and the residue is distributed in water-chloroform. The organic layer is washed with water, dried and concentrated. The residue is purified by recrystallization or chromatography with a solvent, whereby the objective compound (Ie) is obtained.

Table 4 shows the reaction conditions for preparing the compound (Ie) (i.e. structure and amount of the reactants, solvents, reaction time, etc.) and the structure and physical constants of the product (Ie).

TABLE 4

$$\underset{(II)}{\text{[SH-pyridine-N=C(R}^2\text{)-C(R}^3\text{)=O]}} + R^1COCl \longrightarrow \underset{(Ie)}{\text{[S-CO-R}^1\text{-pyridine-N=C(R}^2\text{)-C(R}^3\text{)=O]}}$$
(VII)

| Ex. No. | R² | R³ | R¹ | Amount (g) Compd. (II) | Amount (g) Compd. (VII) | Solvent (ml) | Reaction time (hr) | Compd. No. | Yield (%) | m.p. (°C.) | Molecular Formula | Elementary Analysis, (%) Up: Calcd. Down: Found C | H | N | S | Cl, F, Br |
|---|---|---|---|---|---|---|---|---|---|---|---|---|---|---|---|---|
| 25 | H | CO₂Et | furan-2-yl | 1.5 | 2.0 | Acetone (20) | 2 | Ie-28 | 98.8 | 154–156 | C₁₆H₁₂O₆N₂S | 55.90 55.81 | 3.59 3.51 | 8.13 8.14 | 9.10 9.31 | |
| 26 | H | CO₂Et | 4-Me-phenyl | 0.7 | 0.43 | Acetone (20) | 3 | Ie-29 | 82.5 | 176–178 | C₁₉H₁₆O₄N₂S | 62.03 61.94 | 4.40 4.38 | 7.59 7.60 | 8.70 8.70 | |
| 27 | H | CO₂Et | thiophen-2-yl | 0.6 | 0.39 | Acetone (20) | 1.5 | Ie-30 | 92.6 | 169–170 | C₁₆H₁₂O₄N₂S₂ | 53.04 53.32 | 3.50 3.36 | 7.62 7.77 | 17.93 17.79 | |
| 28 | H | CO₂Et | pyridin-3-yl | 0.3 | 0.21 | Acetone (10) | 24 | Ie-31 | 75.1 | 133–135 | C₁₇H₁₃O₄N₃S | 57.40 57.45 | 3.68 3.69 | 11.67 11.83 | 8.86 9.02 | |
| 29 | H | CO₂Et | 4-MeO-phenyl | 0.4 | 0.3 | Acetone (10) | 2 | Ie-32 | 75.2 | 179–181 | C₁₉H₁₆O₅N₂S | 59.18 59.36 | 4.09 4.20 | 7.17 7.29 | 8.30 8.34 | |
| 30 | H | CO₂Et | 2-Cl-phenyl | 0.4 | 0.3 | Acetone (10) | 1.5 | Ie-33 | 96.5 | 137–140 | C₁₈H₁₃O₄N₂SCl | 55.61 55.60 | 3.51 3.37 | 7.12 7.21 | 8.16 8.25 | 8.97(Cl) 9.12(Cl) |

TABLE 4-continued $$\underset{(II)}{\text{[pyridine-SH with R}^2\text{, R}^3\text{, C=O, N]}} + R^1COCl \longrightarrow \underset{(Ie)}{\text{[pyridine-S-CO-R}^1\text{ with R}^2\text{, R}^3\text{, C=O, N]}}$$
(VII)

| Ex. No. | R² | R³ | R¹ | Amount (g) Compd. (II) | Amount (g) Compd. (VII) | Solvent (ml) | Reaction time (hr) | Compd. No. | Yield (%) | m.p. (°C.) | Molecular Formula | C Calcd/Found | H Calcd/Found | N Calcd/Found | S Calcd/Found | Cl, F, Br |
|---|---|---|---|---|---|---|---|---|---|---|---|---|---|---|---|---|
| 31 | H | CO₂Et | 4-Cl-C₆H₄— | 0.4 | 0.3 | Acetone (10) | 1.5 | Ie-34 | 98.2 | 172–176 | C₁₈H₁₃O₄N₂SCl | 55.39 / 55.60 | 3.34 / 3.37 | 7.18 / 7.21 | 8.21 / 8.25 | 9.06(Cl) / 9.12(Cl) |
| 32 | H | CO₂Et | 3-Cl-C₆H₄— | 0.4 | 0.3 | Acetone (10) | 1 | Ie-35 | 93.3 | 164–168 | C₁₈H₁₃O₄N₂SCl.1/5H₂O | 54.95 / 55.09 | 3.54 / 3.44 | 6.71 / 7.14 | 8.25 / 8.17 | 9.43(Cl) / 9.04(Cl) |
| 33 | H | CO₂Et | Et— | 0.4 | 0.2 | Acetone (10) | 5 | Ie-36 | 77.6 | 116–118 | C₁₄H₁₄O₄N₂S | 54.59 / 54.89 | 4.58 / 4.61 | 9.21 / 9.15 | 10.33 / 10.47 | |
| 34 | H | CO₂Et | Ph—CH₂— | 0.4 | 0.3 | Acetone (10) | 2 | Ie-37 | 76.4 | 122–124 | C₁₉H₁₆O₄N₂S.1/10H₂O | 61.35 / 61.64 | 4.41 / 4.41 | 7.57 / 7.57 | 8.60 / 8.66 | |
| 35 | H | CO₂Et | CH₃(CH₂)₆— | 0.4 | 0.3 | Acetone (10) | 2 | Ie-38 | 51.8 | 65–67 | C₁₈H₂₂O₄N₂S | 59.44 / 59.65 | 6.00 / 6.12 | 7.81 / 7.73 | 8.89 / 8.85 | |
| 36 | H | CO₂Et | cyclopropyl | 0.4 | 0.2 | Acetone (10) | 3 | Ie-39 | 59 | 139–142 | C₁₅H₁₄O₄N₂S.1/5H₂O | 55.86 / 55.96 | 4.45 / 4.51 | 8.71 / 8.70 | 9.99 / 9.96 | |
| 37 | H | CO₂Et | furyl | 0.4 | 0.2 | Acetone (10) | 3 | Ie-40 | 83.8 | 165–172 | C₁₆H₁₂O₅N₂S | 55.62 / 55.81 | 3.63 / 3.51 | 8.18 / 8.14 | 9.21 / 9.31 | |
| 38 | H | CO₂Et | pyridyl | 0.5 | 0.4 | Acetone (10) | 1.5 | Ie-41 | 100 | 186–192d | C₁₇H₁₃O₄N₃S.1/5H₂O | 56.95 / 56.88 | 3.84 / 3.76 | 11.80 / 11.71 | 8.69 / 8.93 | |

TABLE 4-continued $$\underset{(II)}{\text{[structure with SH, N, N, R}^2\text{, R}^3\text{, O]}} + R^1COCl \longrightarrow \underset{(Ie)}{\text{[structure with S-CO-R}^1\text{, N, N, R}^2\text{, R}^3\text{, O]}}$$
(VII)

| Ex. No. | R² | R³ | R¹ | Amount (g) Compd. (II) | Amount (g) Compd. (VII) | Solvent (ml) | Reaction time (hr) | Compd. No. | Yield (%) | m.p. (°C.) | Molecular Formula | Elementary Analysis, (%) Up: Calcd. Down: Found C / H / N / S / Cl, F, Br |
|---|---|---|---|---|---|---|---|---|---|---|---|---|
| 39 | H | CO₂Et | cyclohexyl | 0.4 | 0.3 | Acetone (10) | 1 | Ie-42 | 67.7 | 132–134 | $C_{18}H_{20}O_4N_2S$ | 60.00 / 5.57 / 7.84 / 8.99<br>59.98 / 5.59 / 7.84 / 8.90 |
| 40 | H | CO₂Et | thiophene-CH₂— | 0.4 | 0.3 | Acetone (10) | 1 | Ie-43 | 85.2 | 129–131 | $C_{17}H_{14}O_4N_2S_2 \cdot 1/5H_2O$ | 53.92 / 3.80 / 7.44 / 16.95<br>54.01 / 3.84 / 7.41 / 16.95 |
| 41 | H | CO₂Et | naphthyl | 0.4 | 0.34 | Acetone (10) | 0.5 | Ie-44 | 100 | 161–164 | $C_{22}H_{16}O_4N_2S \cdot 1/5H_2O$ | 64.90 / 3.99 / 6.81 / 7.73<br>64.75 / 4.05 / 6.87 / 7.86 |
| 42 | H | CO₂Et | Ph—O—CH₂— | 0.4 | 0.3 | Acetone (10) | 1 | Ie-45 | 41.2 | 140–142 | $C_{19}H_{16}O_6N_2S$ | 59.46 / 4.16 / 7.34 / 8.39<br>59.36 / 4.20 / 7.29 / 8.34 |
| 43 | H₃ | H | furyl | 0.3 | 0.3 | Acetone (10) | 0.5 | Ie-46 | 47.2 | 219–228d | $C_{14}H_{10}O_3N_2S \cdot 1/10H_2O$ | 58.33 / 3.56 / 9.69 / 11.04<br>58.36 / 3.57 / 9.72 / 11.13 |
| 44 | H | CO₂Et | p-n-Pr-phenyl | 0.4 | 0.3 | Acetone (10) | 0.5 | Ie-47 | 32.7 | 116–117 | $C_{21}H_{20}O_4N_2S$ | 63.33 / 5.07 / 6.81 / 8.18<br>63.62 / 5.09 / 7.07 / 8.09 |

TABLE 4-continued

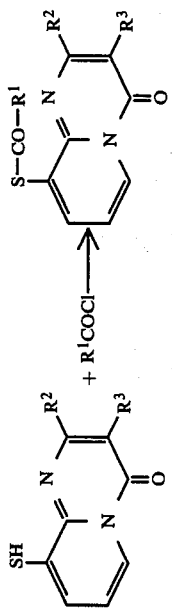

| Ex. No. | R² | R³ | R¹ | Amount (g) Compd. (II) | Amount (g) Compd. (VII) | Solvent (ml) | Reaction time (hr) | Compd. No. | Yield (%) | m.p. (°C.) | Molecular Formula | Elementary Analysis, (%) Up: Calcd. Down: Found C | H | N | S | Cl, F, Br |
|---|---|---|---|---|---|---|---|---|---|---|---|---|---|---|---|---|
| 45 | H | CO₂Et | 2,4-dichlorophenyl | 0.4 | 0.4 | Acetone (10) | 0.5 | Ie-48 | 70.7 | 171–173 | $C_{18}H_{12}O_4N_2SCl_2$ | 50.85 / 51.07 | 2.99 / 2.86 | 6.51 / 6.62 | 7.61 / 7.58 | 16.68(Cl) / 16.75(Cl) |
| 46 | H | CO₂Et | cinnamyl | 0.4 | 0.3 | Acetone (10) | 3 | Ie-49 | 80.8 | 175–178 | $C_{20}H_{16}O_4N_2S.1/10H_2O$ | 62.63 / 62.84 | 4.13 / 4.27 | 7.17 / 7.33 | 8.31 / 8.39 | |
| 47 | H | CO₂Et | 4-bromophenyl | 0.4 | 0.35 | Acetone (10) | 1 | Ie-50 | 52.1 | 173–175 | $C_{18}H_{13}O_4N_2SBr$ | 49.77 / 49.89 | 3.10 / 3.02 | 6.51 / 6.47 | 7.57 / 7.40 | 18.13(Br) / 18.44(Br) |
| 48 | H | CO₂Et | 3-CF₃-phenyl | 0.4 | 0.34 | Acetone (10) | 1 | Ie-51 | 35.4 | 122–124 | $C_{19}H_{13}O_4N_2SF_3$ | 54.03 / 54.08 | 3.10 / 3.14 | 6.63 / 6.78 | 7.59 / 7.82 | 13.50(F) / 13.39(F) |
| 49 | H | CO₂Et | 4-cyanophenyl | 0.4 | 0.26 | Acetone (10) | 1.5 | Ie-52 | 49.5 | 152–155 | $C_{19}H_{13}O_4N_3S$ | 59.94 / 60.15 | 3.52 / 3.45 | 10.87 / 11.08 | 8.26 / 8.45 | |
| 50 | H | CO₂Et | 3-nitrophenyl | 0.4 | 0.3 | Acetone (10) | 1 | Ie-53 | 72.1 | 147–149 | $C_{18}H_{13}O_6N_3S.1/5H_2O$ | 53.75 / 53.65 | 3.26 / 3.35 | 10.41 / 10.43 | 7.99 / 7.96 | |

EXAMPLE 51

Preparation of 3-ethoxycarbonyl-9-[[(5-methylisoxyazol-3yl)-carbonyl]thio]-4H-pyrido[1,2-a]pyrimidin-4-one Ie-54.

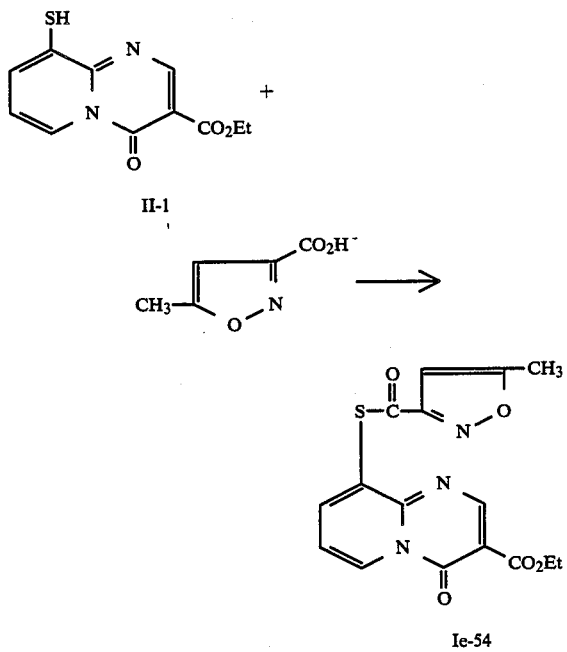

To a solution of 0.23 g of 3-carboxy-5-methylisoxazole in 5 ml of dry benzene are added 0.39 g of thionyl chloride and then 3 drops of DMF. The resultant mixture is refluxed on an oil bath for 5 hours and concentrated in vacuo. The residue is dissolved in 10 ml of acetone and mixed with 1.1 g of powdery potassium carbonate and 0.4 g of 3-ethoxycarbonyl-9-mercapto-4H-pyrido[1,2-a]pyrimidin-4-one II-1, and the mixture is stirred at room temperature for 1 hour. The reaction mixture is concentrated in vacuo and, the residue is chromatographed on a column of silica gel which is eluted with ethyl acetate. Concentration of the eluate affords 0.2 g of the titled compound.

Yield: 33.8%, m.p.: 147°–150° C. (recrystallized from chloroform-n-hexane),

Anal. Calcd. for $C_{16}H_{13}O_5N_3S \cdot \frac{1}{2}H_2O$ C, 52.17; H, 3.93; N, 11.41; S, 8.71(%), Found: C, 52.42; H, 3.69; N, 11.32; S, 8.87(%).

EXAMPLE 52

Preparation of 3-ethoxycarbonyl-9-[[(5-cyclopropylisoxazol-3-yl)carbonyl]thio]-4H-pyrido[1,2-a]pyrimidin-4-one Ie-55.

To a solution of 0.28 g of 3-carboxy-5-cyclopropylisoxazole in 5 ml of dry benzene are added 0.39 g of thionyl chloride and then 3 drops of DMF. The resultant mixture is refluxed on an oil bath for 5 hours and concentrated in vacuo. The residue is dissolved in 10 ml of acetone and mixed with 1.1 g of powdery potassium carbonate and 0.4 g of 3-ethoxycarbonyl-9-mercapto-4H-pyrido[1,2-a]pyridin-4-one. The resultant mixture is stirred at room temperature for 1 hour and concentrated in vacuo. The residue is dissolved in chloroform, and the solution is filtered to remove the insoluble material. The filtrate is concentrated in vacuo to dryness, and the residue is recrystallized from chloroform-n-hexane to give 0.32 g of the title compound Ie-55.

Yield: 52%, m.p.: 189°–191° C. (dec.),

Anal. Calcd. for $C_{16}H_{15}O_5N_3S \cdot 1/5H_2O$ C, 55.57; H, 3.99; N, 10.80; S, 8.24(%), Found: C, 55.53; H, 3.99; N, 10.72; S, 8.17(%).

EXAMPLE 53

Preparation of 3-ethoxycarbonyl-9-(4-ethoxycarbonylbenzoyl)thio-4H-pyrido[1,2-a]pyrimidin-4-one Ie-56.

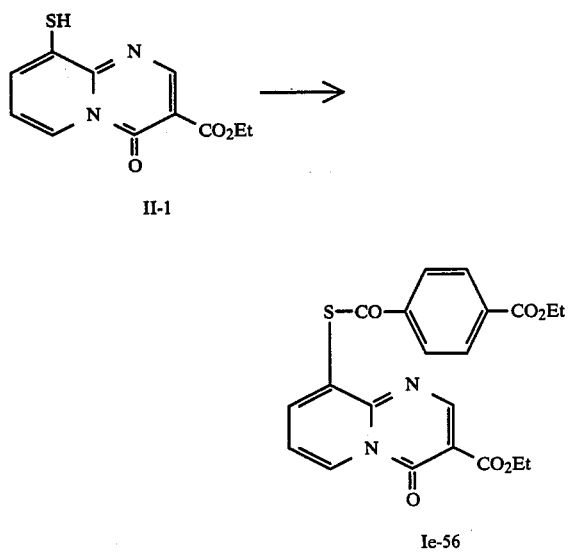

To a mixture of 1.47 g (2.4 mmol) of 4-ethoxycarbonylbenzoic acid, 3 drops of DMF and 10 ml of benzene is added 0.52 g (4.4 mmol) of thionyl chloride, and the resultant mixture is refluxed for 3 hours under stirring and concentrated in vacuo to dryness. The residue is dissolved in acetone and mixed with 1.4 g of solid potassium carbonate and then 0.5 g (2 mmol) of 3ethoxycarbonyl-9-mercapto-4H-pyrido[1,2-a]pyrimidin-4-one II-1, and the resultant mixture is vigorously stirred at room temperature for 20 minutes. The reaction mixture is concentrated in vacuo to dryness, and the residue is distributed in chloroformwater. The organic layer is dried over sodium sulfate and concentrated in vacuo. The residue is chromatographed on a column of silica gel, which is eluted with ethyl acetate to give 0.9 g of the titled compound Ie-56.

Yield: about 100%, m.p.: 146°–148° C. (chloroform-n-hexane),

Anal. Calcd. for $C_{21}H_{18}N_2O_6S$ C, 59.14; H, 4.25; N, 6.57; S, 7.52,

Found: C, 59.92; H, 4.23; N, 6.55; S, 7.44.

EXAMPLE 54-57

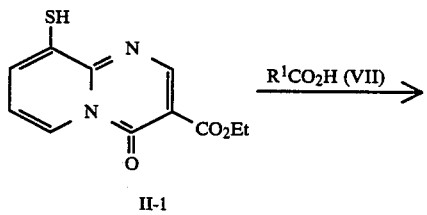

$R^1CO_2H$ (VII) →

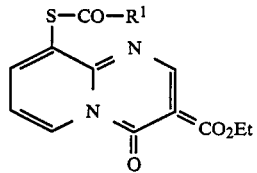

(Ie)

To a suspension or solution of the substituted arylcarboxylic acid (VII) in an appropriate solvent (Solvent a) are added a catalytic amount of DMF and then thionyl chloride, and the resultant mixture is refluxed for about 1-5 hours (reaction time $h_1$) and concentrated in vacuo to dryness. The residue is dissolved in an appropriate solvent (Solvent b) and mixed with appropriate base and 3-ethoxycarbonyl-9-mercapto-4H-pyrido[1,2-a]pyrimidin-4-one (II-1), and the resultant mixture is stirred at room temperature for about 0.5-3 hours (reaction time $h_2$). The reaction mixture is concentrated in vacuo to dryness, and the residue is distributed in chloroform-water. The organic layer is washed with water, dried and concentrated. The residue is purified by recrystallization or chromatography on silica gel with appropriate solvent.

Table 5 shows the reaction conditions (i.e. structure and amount of the reactant, solvent, reaction time etc.) and the structure and physical constants of the product (Ie).

TABLE 5

$$\text{(II)} + R^1CO_2H \text{ (VII)} \longrightarrow \text{(Ie)}$$

| Ex No | R² | R³ | R¹ | Amount Compd. (VII) (g) | Amount Compd. (II) (g) | SOCl₂ (ml) | K₂CO₃ (g) | Solvent (ml) (a) | Solvent (ml) (b) | Reaction time (hr) h₁ | Reaction time (hr) h₂ | Yield (%) | Compd. No. | m.p. (°C.) | Molecular Formula | Elementary Analysis (%) Up: Found Down: Calcd. C | H | N | S |
|---|---|---|---|---|---|---|---|---|---|---|---|---|---|---|---|---|---|---|---|
| 54 | H | CO₂Et | (thiophene) | 0.23 | 0.4 | 0.23 | 1.1 | 5 | 10 | 5 | 1 | 56.8 | Ie-57 | 149–151 | C₁₆H₁₂O₄N₂S₂ | 53.18 53.32 | 3.42 3.36 | 7.77 7.77 | 17.67 17.79 |
| 55 | H | CO₂Et | PhCH₂O–/MeO– phenyl isoxazole | 0.57 | 0.4 | 0.23 | 1.1 | 5 | 15 | 5 | 0.5 | 44.9 | Ie-58 | 196–207 (d) | C₂₉H₂₃O₇N₃S ·1/5H₂O | 62.01 62.07 | 4.20 4.20 | 7.43 7.49 | 5.55 5.71 |
| 56 | H | CO₂Et | CO₂Me-phenyl | 0.43 | 0.5 | 0.32 | 1.4 | 10 | 10 | 3 | 1 | 100 | Ie-59 | 201–206 (d) | C₂₀H₁₆O₆N₂S ·1/5H₂O | 57.59 57.74 | 3.82 3.97 | 6.80 6.73 | 7.52 7.71 |
| 57 | H | CO₂Et | CH₃CO-phenyl | 0.39 | 0.5 | 0.32 | 1.4 | 10 | 20 | 2 | 1 | 25.3 | Ie-60 | 182–185 (d) | C₂₀H₁₆N₂O₅S ·1/5H₂O | 60.21 60.05 | 4.18 4.13 | 6.99 7.00 | 7.94 8.02 |

EXAMPLE 58

Preparation of 3-ethoxycarbonyl-9-(4-sulfamoylbenzoyl)thio4H-pyrido[1,2-a]pyrimidin-4-one Ie-61.

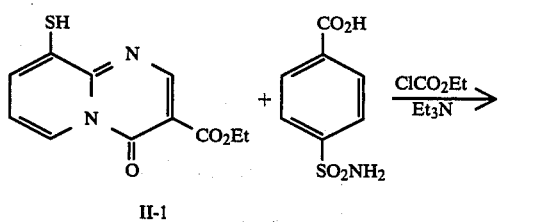

II-1

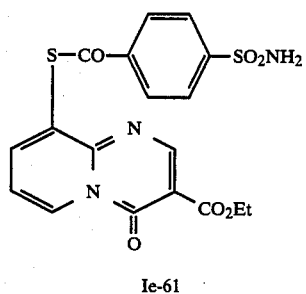

Ie-61

To a solution of 0.48 g (2.4 mmol) of 4-sulfamoylbenzoic acid in 10 ml of DMF are added 0.29 g of Et₃N and then 0.28 g ethyl chloroformate, and the mixture is stirred at room temperature for 1 hour and mixed with 0.5 g of solid 3-ethoxycarbonyl-9-mercapto-4H-pyrido[1,2-a]pyrimidin-4-one II-1. The mixture is stirred at room temperature for 2 hours, diluted with 100 ml of water and shaken with ethyl acetate. The organic layer is washed with water, dried and concentrated in vacuo. The residue is washed with ethyl acetate to give 0.68 g of the titled compound.

Yield: 78.5%, m.p.: 214°–217° C. (dec.) (ethyl acetate-tetrahydrofuran),

Anal. Calcd. for $C_{18}H_{15}N_3O_6S_2$ C, 49.87; H, 3.49; N, 9.70; S, 14.80(%), Found: C, 49.86; H, 3.57; N, 9.49; S, 14.64(%).

EXAMPLE 59–62

To a suspension or solution of the substituted arylcarboxylic acid (VII) in appropriate solvent are added appropriate base and then ethyl chloroformate, and the resultant mixture is stirred at 0° C. to room temperature for about 0.5–2 hours (reaction time $h_1$). 3-Ethoxycarbonyl-9-mercapto-4H-pyrido[1,2-a]pyrimidin-4-one II-1 is added in the form of solid or solution in appropriate solvent to the mixture, which is stirred at 0°–100° C. for about 0.5–5 hours (reaction time $h_2$). The reaction mixture is distributed in water and appropriate organic solvent. The organic layer is washed with water, dried and concentrated in vacuo to dryness. The residue is purified by recrystallization or chromatography on silica gel, whereby the product (Ie) is obtained.

Table 6 shows the reaction conditions (i.e. structure and amount of the reactants, solvent, reaction time, etc.) and the structure and physical constants of the product (Ie).

TABLE 6
$$\text{(II)} + R^1CO_2H \text{ (VII)} \longrightarrow \text{(Ie)}$$
| Ex No | R² | R³ | R¹ | Amount (g) Compound (III) | (II) | Amount of Solvents (ml) ClCO₂Et | Et₃N | DMF | Reaction time (hr) h₁ | h₂ | Yield (%) | Compd. No. | m.p. (°C.) | Molecular Formula | Elementary Analysis (%) Up: Found Down: Calcd. C | H | N | S |
|---|---|---|---|---|---|---|---|---|---|---|---|---|---|---|---|---|---|---|
| 59 | H | CO₂Et | 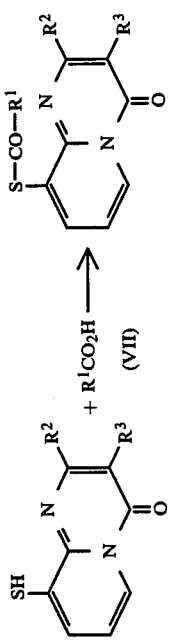 | 0.48 | 0.5 | 0.25 | 0.4 | 10 | 1 | 1 | 56.6 | Ie-62 | 204–210 (d) | C₁₉H₁₆N₂O₆S₂ | 52.54 52.76 | 3.83 3.73 | 6.46 6.48 | 14.76 14.83 |
| 60 | H | CO₂Et | 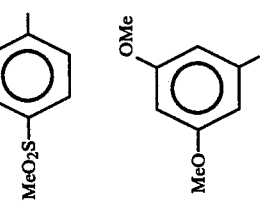 | 0.44 | 0.5 | 0.25 | 0.4 | 10 | 1 | 1 | 50.4 | Ie-63 | 164–166 | C₂₀H₁₈N₂O₆S | 57.88 57.96 | 4.43 4.38 | 6.76 6.76 | 7.50 7.74 |
| 61 | H | CO₂Et | 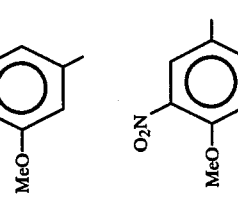 | 0.47 | 0.5 | 0.25 | 0.4 | 10 | 1 | 1 | 81.6 | Ie-64 | 216–222 (d) | C₁₉H₁₆N₃O₇S | 53.16 53.14 | 3.59 3.52 | 9.61 9.79 | 7.28 7.47 |
| 62 | H | CO₂Et | 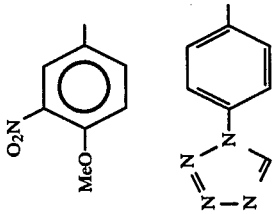 | 0.5 | 0.5 | 0.28 | 0.44 | 10 | 1 | 1.5 | 31.9 | Ie-65 | 233–236 (d) | C₁₉H₁₄N₆O₄S | 53.92 54.02 | 3.41 3.34 | 19.78 19.90 | 7.37 7.59 |

EXAMPLE 63

Preparation of 3-ethoxycarbonyl-9-(4-methoxycarbonylbenzoyl)thio-4H-pyrido[1,2-a]pyrimidin-4-one Ie-66.

To a mixture of 30 g of 3-ethoxycarbonyl-9-mercapto-4H-pyrido[1,2-a]pyrimidin-4-one II-1, 2.49 g of powdery potassium carbonate and 500 ml of acetone is added 23.8 g of 4-methoxycarbonylbenzoyl chloride with stirring, and the resultant mixture is stirred at room temperature for 1 hour. The reaction mixture is concentrated to dryness in vacuo and the residue is distributed in water-chloroform. The chloroform layer is washed with saturated brine, dried over sodium sulfate and concentrated in vacuo. The residue is recrystallized from ethyl acetate to give 43 g of the titled compound Ie-66.

Yield: 86.9%, m.p.: 174°–176° C.,

Anal. Calcd. for $C_{20}H_{16}N_2O_6S$ C, 58.24; H, 3.91; N, 6.79; S, 7.78(%),

Found: C, 58.39, H, 4.00; N, 6.81; S, 7.84(%).

EXAMPLE 64–74

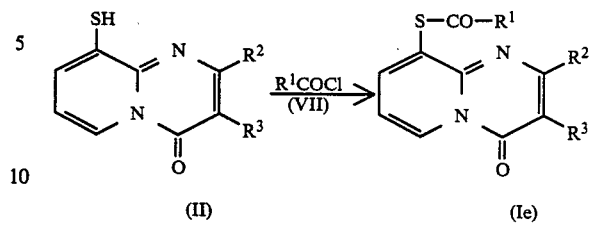

To a suspension or solution of 9-mercapto-4H-pyrido[1,2-a]pyrimidin-4-one (II) in appropriate solvent are added appropriate base and then the acid chloride (VII), and the mixture is stirred at room temperature for about 1–5 hours. The reaction mixture is concentrated to dryness in vacuo and the residue is distributed in water-chloroform. The organic layer is washed with water, dried and concentrated in vacuo. The residue is purified by recrystallization from appropriate solvent or chromatography on silica gel, whereby the product (Ie) is obtained.

Table 7 shows the reaction conditions and the structure and the physical constants of the products (Ie).

TABLE 7

$$\underset{(II)}{\underset{\text{SH}}{\bigcirc}\!\!\!-\!\!\!\underset{H}{\overset{N}{\bigcirc}}\!\!\!\underset{O}{\overset{R^2}{\underset{R^3}}}} + R^1COCl \longrightarrow \underset{(Ie)}{\underset{\text{S-CO-R}^1}{\bigcirc}\!\!\!-\!\!\!\underset{N}{\overset{N}{\bigcirc}}\!\!\!\underset{O}{\overset{R^2}{\underset{R^3}}}}$$

(VII)

| Ex No | $R^2$ | $R^3$ | $R^1$ | Amount (g) Compd. (II) | Amount (g) Compd. (VII) | Acetone (ml) | Reaction time (min) | $K_2CO_3$ (g) | Yield (%) | Compd. No. | m.p. (°C) | Molecular Formula | Elementary Analysis (%) Up: Found / Down: Calcd. C | H | N | S | Halogen |
|---|---|---|---|---|---|---|---|---|---|---|---|---|---|---|---|---|---|
| 64 | H | $CO_2Et$ | $-CH_2-C_6H_4-Br$ (p) | 0.4 | 0.37 | 10 | 45 | 0.33 | 60.8 | Ie-67 | 135–137 | $C_{19}H_{16}O_4N_2SBr$ | 50.89 / 51.01 | 3.46 / 3.38 | 6.07 / 6.26 | 6.90 / 7.17 | 17.76 / 17.86 |
| 65 | H | $CO_2CH_2Ph$ | $-CH_2-C_6H_5$ | 0.985 | 0.5 | 50 | 120 | 0.5 | 67.9 | Ie-68 | 126–137 | $C_{24}H_{18}O_4N_2S$ | 66.94 / 66.96 | 4.15 / 4.21 | 6.52 / 6.51 | 7.38 / 7.45 | |
| 66 | H | $CO_2CH_2Ph$ | $-C_6H_4-CO_2Me$ (p) | 0.7 | 0.5 | 20 | 50 | 0.4 | 61.5 | Ie-69 | 159–160 | $C_{26}H_{18}O_6N_2S$ | 62.99 / 63.28 | 4.02 / 3.82 | 5.88 / 5.90 | 6.58 / 6.76 | |
| 67 | H | $CO_2CH_2Ph$ | cyclohexyl | 0.6 | 0.33 | 20 | 60 | 0.3 | 26.1 | Ie-70 | 138–139 | $C_{23}H_{22}O_4N_2S$ | 65.31 / 65.39 | 5.15 / 5.25 | 6.57 / 6.63 | 7.61 / 7.59 | |
| 68 | H | $CO_2Et$ | $-CH_2-C_6H_4-CH_3$ (p) | 0.4 | 0.27 | 10 | 40 | 0.33 | 85.1 | Ie-71 | 118–121 (d) | $C_{20}H_{18}O_4N_2S \cdot 1/10H_2O$ | 62.47 / 62.51 | 4.60 / 4.77 | 7.26 / 7.29 | 8.28 / 8.35 | |
| 69 | H | $CO_2Et$ | $-CH_2-C_6H_4-Cl$ (p) | 0.4 | 0.3 | 10 | 40 | 0.33 | 69.9 | Ie-72 | 136–138 | $C_{19}H_{15}O_4N_2SCl$ | 56.56 / 56.64 | 3.68 / 3.75 | 7.03 / 6.95 | 7.86 / 7.96 | 8.75 / 8.80 |
| 70 | H | $CO_2Et$ | $-S-CH_2CH=CH_2$ | 0.4 | 0.24 | 10 | 30 | 0.33 | 54.6 | Ie-73 | 80–82 | $C_{15}H_{14}O_4N_2S_2 \cdot 1/5H_2O$ | 50.76 / 50.89 | 4.06 / 4.10 | 7.86 / 7.91 | 17.99 / 18.21 | |

TABLE 7-continued
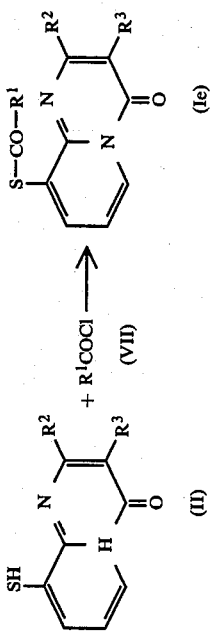
| Ex No | R² | R³ | R¹ | Amount (g) Compd. (II) | Amount (g) Compd. (VII) | Acetone (ml) | Reaction time (min) | K₂CO₃ (g) | Yield (%) | Compd. No. | m.p. (°C.) | Molecular Formula | Elementary Analysis (%) Up: Found Down: Calcd. C | H | N | S | Halogen |
|---|---|---|---|---|---|---|---|---|---|---|---|---|---|---|---|---|---|
| 71 | H | CO₂Et | 2,6-Cl₂-C₆H₃ | 0.4 | 0.33 | 10 | 60 | 0.33 | 71.5 | Ie-74 | 169–172 | $C_{18}H_{12}O_4N_2SCl_2$ | 50.89 51.07 | 2.98 2.86 | 6.54 6.62 | 7.46 7.58 | 16.88 16.75 |
| 72 | H | CO₂Et | 4-F-C₆H₄ | 0.5 | 0.35 | 20 | 40 | 0.41 | 80.7 | Ie-75 | 191–196 (d) | $C_{18}H_{13}O_4N_2SF$ | 57.86 58.06 | 3.56 3.52 | 7.34 7.52 | 8.75 8.51 | 5.29 5.10 |
| 73 | H | CO₂Et | 2-AcO-C₆H₄ | 0.5 | 0.44 | 10 | 60 | 0.41 | 58.3 | Ie-76 | 129–131 | $C_{20}H_{16}O_6N_2S$ | 58.24 58.17 | 3.91 4.03 | 6.79 6.74 | 7.78 7.61 | |
| 74 | H | CO₂CH₂-C₆H₄-OMe | —NMe₂ | 0.5 | 0.4 | 20 | 60 | 0.5 | 80 | Ie-77 | 153–154 | $C_{20}H_{19}O_6N_3S$ | 57.98 58.10 | 4.75 4.63 | 10.07 10.16 | 7.64 7.77 | |

EXAMPLE 75

Preparation of 9-(dimethylcarbamoyl)thio-4H-pyrido-[1,2-a]pyrimidin-4-one Ib-78.

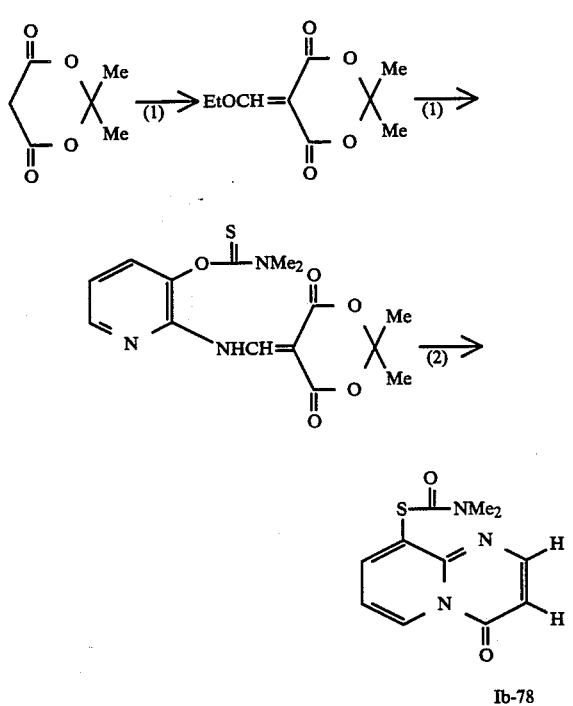

Ib-78

1. A mixture of 6.0 g of 2,2-dimethyl-1,3-dioxane-4,6dione and 30 ml of ethyl orthoformate is refluxed on an oil bath for 2 hours, mixed with 8.0 g of 2-amino-3-dimethylthiocarbamoyloxypyridine and again refluxed for 2 hours under stirring. After cooling, the precipitated crystal is filtered and washed with ether to give 6.4 g of 2-(2,2-dimethyl-4,6-dioxo-1,3-dioxan-5-ylidenemethyl)amino-3-dimethylthiocarbamoyloxypyridine. The product is recrystallized from ethyl acetate.

m.p.: 223°–225° C. (dec),

Anal. Calcd. for $C_{15}H_{17}O_5N_3S$, C, 51.27; H, 4.88; N, 11.96; S, 9.12(%), Found: C, 51.29; H, 4.78; N, 11.84; S, 8.99(%).

2. A solution of 2.5 g of the above product in 100 ml of Dowtherm A (Dow Chemical Co.) is refluxed for 5 minutes.

After cooling, the reaction mixture is chromatographed on a column of silica gel, eluting at first Dowtherm A with n-hexane and then 1.4 g of the titled compound Ib-78 with ethyl acetate.

m.p. 151°–152° C. (ethyl acetate),

Anal. Calcd. for $C_{11}H_{11}O_2N_3S$, C, 53.00; H, 4.45; N, 16.86; S, 12.86(%), Found: C, 52.89; H, 4.36; N, 16.74; S, 12.83(%).

EXAMPLE 76

Preparation of 9-(benzyloxycarbonyl)thio-3-carboxy-4H-pyrido[1,2-a]pyrimidin-4-one Ie-80.

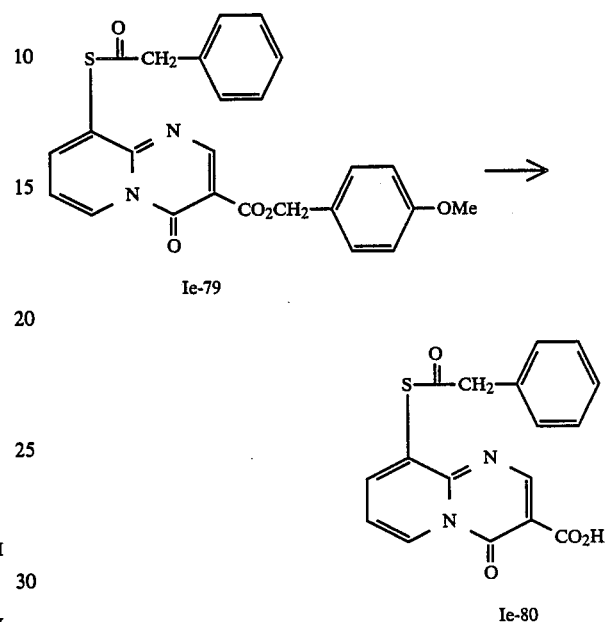

A mixture of 0.872 g of 9-(benzylcarbonyl)thio-3-(4-methoxybenzyloxycarbonyl)-4H-pyrido[1,2-a]pyrimidin-4-one Ie-79, 2.5 g of anisole and 10 ml of dry methylene chloride is cooled with ice water, mixed with 5 ml of trifluoroacetic acid and stirred under cooling with ice water for 3 hours. The reaction mixture is concentrated to dryness in vacuo, and the residue is recrystallized from ethyl acetate to give the titled compound Ie-80.

Anal. Calcd. for $C_{17}H_{12}O_4N_2S$ C, 59.99; H, 3.55; N, 8.23; S, 9.42(%),

Found: C, 60.00; H, 3.68; N, 8.20; S, 9.27(%).

EXAMPLE 77

Preparation of 3-carboxy-9-(dimethylcarbamoyl)thio-4Hpyrido[1,2-a]pyrimidin-4-one Ib-81.

A mixture of 0.508 g of 9-(dimethylcarbamoyl)thio-3-(4-methoxybenzyloxycarbonyl)-4H-pyrido[1,2-a]pyrimidin-4-one Ib-82, 2,5 g of anisole and 5 ml of dry methylene chloride is cooled with ice water, mixed with 5 ml of trifluoroacetic acid and stirred under cooling with ice water for 3 hours. The reaction mixture is concentrated in vacuo to dryness, and the residue is washed with ether to give 0.32 g of crude product, which is recrystallized from 95% ethanol to give the titled compound Ib-81.

m.p.: 223°–224° C.,

Anal. Calcd. for $C_{12}H_{11}O_4N_3S$ C, 49.14; H, 3.78; N, 14.33; S, 10.93(%), Found: C, 49.08; H, 3.80; N, 14.24; S, 10.98(%).

EXAMPLE 78

Preparation of
9-mercapto-3-(4-methoxybenzyloxy)-4H-pyrido[1,2-a]pyrimidin-4-one II-2.

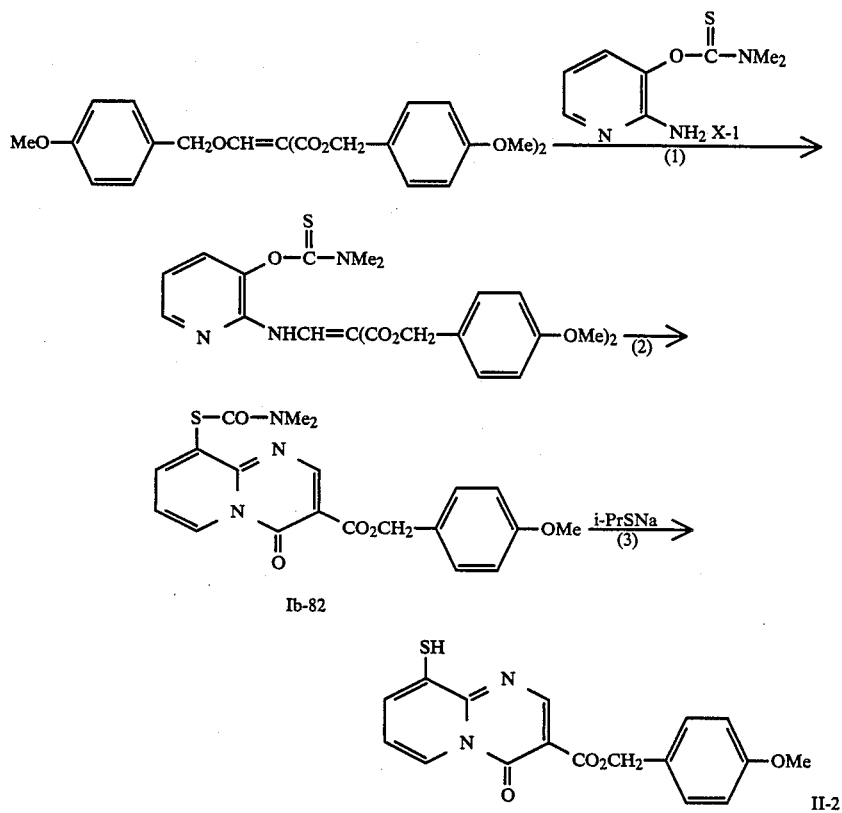

1. A mixture of 14.4 g of di(4-methoxybenzyl)-4-methoxybenzyloxymethylenemalonate and 5.9 g of 2-amino-3-(dimethylthiocarbamoyloxy)pyridine X-1 is heated at 120° C. on an oil bath for 1 hour under stirring. The reaction mixture is chromatographed on a column of silica gel, eluting with n-hexane-ethyl acetate (1:1 v/v), whereby 13.3 g of 3-dimethylthio-carbamoyloxy-2-[2,2-bis(4-methoxybenzyloxycarbonyl)ethenylamino]pyridine is obtained.

m.p. 117°–118° C. (ethyl acetate-ether),

Anal. Calcd. for $C_{28}H_{29}O_7N_3S$ C, 60.97; H, 5.30; N, 7.62; S, 5.81(%),

Found: C, 60.91; H, 5.31; N, 7.55; S, 5.80(%).

2. A solution of 11 g of the above product in 100 ml of diphenyl ether is refluxed for half an hour. After cooling, the reaction mixture is dissolved and chromatographed on a column of silica gel, eluting at first diphenyl ether with n-hexane for removal and then 4.3 g of 9-dimethylcarbamoylthio-3-(4-methoxybenzyloxycarbonyl)-4H-pyrido[1,2-a]pyrimidin-4-one Ib-82 with ethyl acetate.

m.p. 153°–154° C. (ethyl acetate),

Anal. Calcd. for $C_{20}H_{19}O_5N_3S$ C, 58.10; H, 4.63; N, 10.16; S, 7.75(%),

Found: C, 57.98; H, 4.75; N, 10.07; S, 7.64(%).

3. To a suspension of 0.5 g of NaH in 50 ml of tetrahydrofuran is dropwise added 1.13 ml of n-propyl mercaptan at room temperature in a nitrogen stream, and the resultant mixture is stirred for 1 hour. Then a solution of 4.3 g of the product (obtained in (2)) in 300 ml is added in one portion to the mixture. The reaction mixture is stirred at room temperature for 24 hours, mixed with 0.9 g of acetic acid and concentrated to dryness in vacuo. The residue is distributed in chloroform-water. The organic layer is collected, washed with water, dried and concentrated in vacuo. The residue is washed with ether-ethyl acetate to give 1.8 g of the titled compound II-2 as reddish brown crystals.

m.p. above 230° C.

EXAMPLE 79

Preprartion of
9-(benzylcarbonyl)thio-3-ethoxycarbonyl-4Hpyrido[1,2-a]pyrimidin-4-one Ie-84

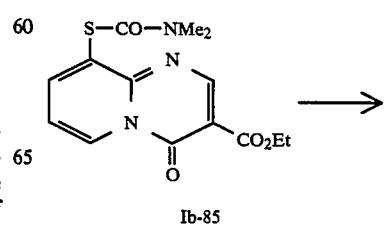

Ib-85

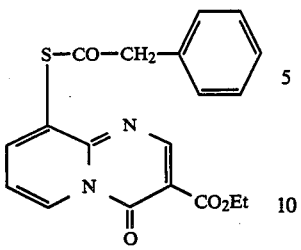

Ie-84

To a solution of 0.129 g of 9-(dimethylcarbamoyl)thio-3ethoxycarbonyl-4H-pyrido[1,2-a]pyrimidin-4-one Ib-85 in 5 ml of 1,2-dichloroethane are added 65 μl of phenylacetyl chloride and 0.13 g of zinc iodide, and the resultant mixture is refluxed in a nitrogen stream for 45 minutes. After cooling, the reaction mixture is shaken with N-hydrochloric acid and the organic layer is washed with saturated brine in order, dried and concentrated in vacuo. The residue is chromatographed on a column of silica gel, eluting with ethyl acetate, whereby 0.118 g of the titled compound Ie-84 is obtained.

Yield: 58%,
m.p.: 126°–128° C.,
Anal. Calcd. for $C_9H_{16}N_2O_4S$ C, 61,94; H, 4.38; N, 7.60; S, 8.70(%),
Found: C, 62.09; H, 4.29; N, 7.48; S, 8.64(%).

REFERENTIAL EXAMPLE 1

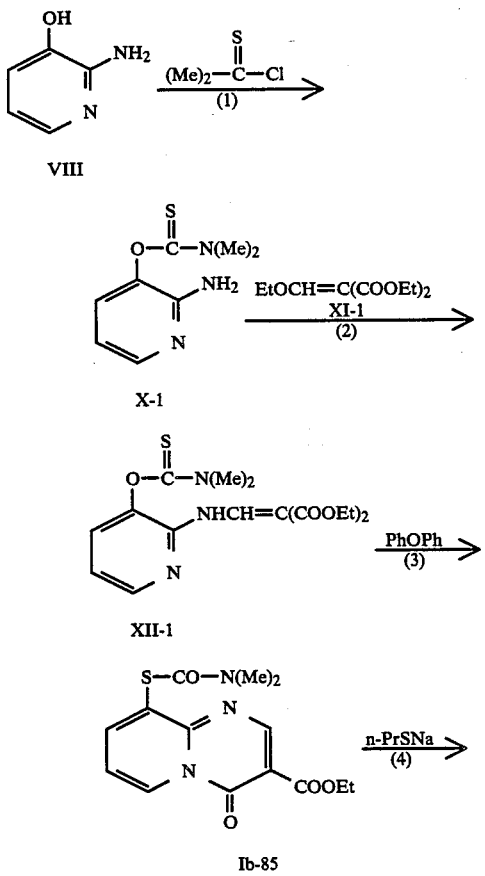

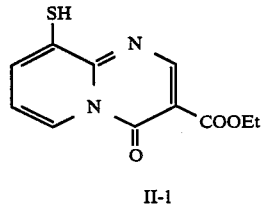

II-1

1. Preparation of 2-amino-3-dimethylthiocarbamoylpyrimidine X-1.

To a solution of 45 g of 2-amino-3-hydroxypyrimidine VIII in 700 ml of acetone is added 58 g of powdered $K_2CO_3$ and the mixture is stirred. 49 g of dimethylthiocarbamoyl chloride is added to the mixture, which is stirred at room temperature for 48 hours. Insoluble material is filtered, washed with acetone, and both the resultant solvent and the filtrate are evaporated. The residue is purified by silica gel chromatography to give 44.2 g of the titled compound X-1 from the fractions eluted with AcOEt.

Yield: 54.8%,
m.p.: 134°–136° C. (recrystallized from AcOEt),
Anal. Calcd. for $C_8H_{11}ON_3S$ C,48.71; H,5.62; N,21.30; S,16.25(%),
Found: C,48.43; H,5.59; N,20.77; S,16.29(%).

2. Preparation of 2-[2′,2′-bis(ethoxycarbonyl)ethyleneamino]-3-(N′,N′-dimethylthiocarbamoyloxy)pyridine XII-1.

13.7 g of the compound X-1 provided in the said item (1) and 14 g of diethyl ethoxymethylenemalonate XI-1 are heated at 100° C. for 1 hour. The reaction mixture is purified by silica gel chromatography to give 19.3 g of the titled compound XII-1 from the fractions eluted with the mixture of benzene and AcOEt (4:1 v/v %).

m.p.: 91°–92.5° C. (recrystallized from ether),
Anal. Calcd. for $C_{16}H_{21}O_6N_3S$ C,52.30; H,5.76; N,11.44; S,8.73(%),
Found: C,52.37; H,5.82; N,11.48; S,8.50(%).

3. Preparation of 3-ethoxycarbonyl-9-dimethylcarbamoylthio4H-pyrido[1,2-a]pyrimidin-4-one Ib-85.

To a solution of 8.0 g of the compound XII-1 provided in the said item (2) in 20 ml of ether is heated under reflux for 30 minutes in an oil bath. The reaction mixture is poured into 1 L of n-hexane, and the crystal precipitated is filtered, and purified by silica gel chromatography to give 4.0 g of the titled compound Ib-85 from the fractions eluted with AcOEt.

Yield: 53%,
m.p.: 133°–134° C. (recrystallized from AcOEt),
Anal. Calcd. for $C_{14}H_{16}O_4N_3S$ C,52.33; H,4.71; N,13.08; S,9.98(%),
Found: C,52.13; H,4.66; N,12.99; S,9.75(%).

4. Preparation of 3-ethoxycarbonyl-9-mercapto-4H-pyrido[1,2-a]pyrimidin-4-one II-1

To a suspension of 0.3 g NaH in 30 ml of anhydrous THF is added dropwise 0.6 g of n-propyl mercaptan at 0° C. in a stream of nitrogen, and the mixture is stirred for 15 minutes. A solution of 2.0 g of the compound Ib-85 provided in the said item (3) in 100 ml of anhydrous THF is added to the mixture, which is stirred at room temperature for 8 hours. The resultant mixture is allowed to stand overnight. The reaction mixture is mixed with 0.5 g of acetic acid and concentrated to dryness in vacuo. The residue is mixed with about 150 ml of water and stired to give 1.3 g of the titled compound II-1.

Yield: 81%,
m.p.: 151°-152° C. (recrystallized from AcOEt),
Anal. Calcd. for $C_{11}H_{10}O_3N_2S$ C,52.79; H,4.03; N,11.19; S,12.81(%),
Found: C,52.88; H,3.97; N,11.24; S,12.66(%).

REFERENTIAL EXAMPLE 2

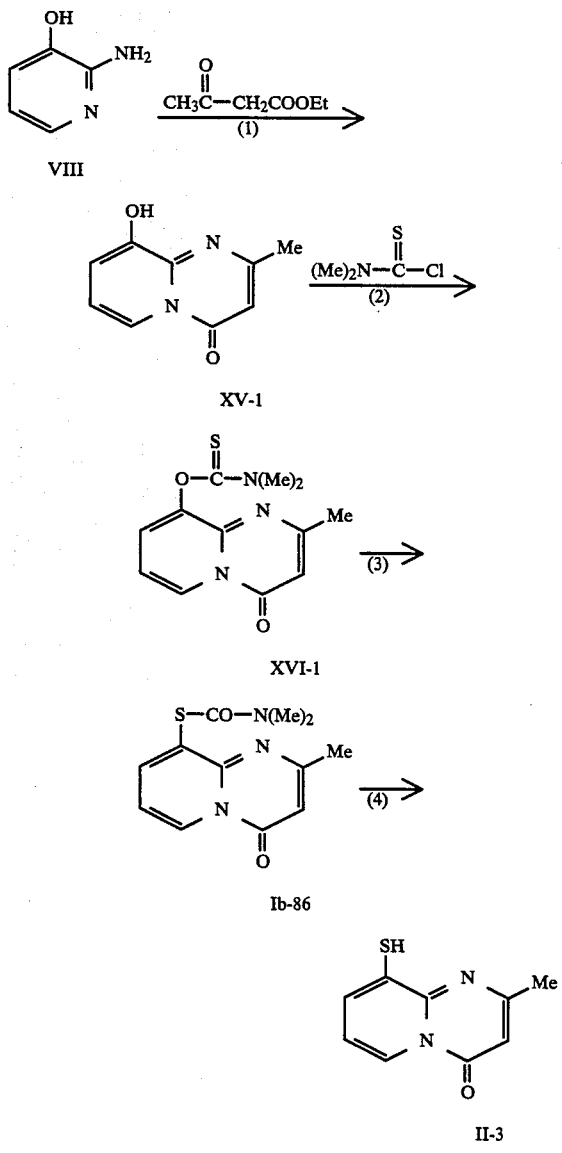

1. Preparation of 9-hydroxy-2-methyl-4H-pyrido[1,2-a]pyrimidin-4-one XV-1.

To a mixture of 1.1 g of 2-amino-3-hydroxypyridine VIII and 1.1 g of etyl acetoacetate is added 4 ml of polyphosphoric acid and the resultant mixture is stirred under heating at 100° C. for 4 hours. The reaction mixture is poured into ice water, and the resulting solution is adjusted to PH 4 with 2N aqueous sodium hydroxide, then to PH 7 with aqueous sodium carbonate and shaken with $CHCl_3$. The organic layer is washed with water and dried over anhydrous sodium sulfate. The solvent is evaporated to give 0.9 g of the titled compound XV-1.

Yield: 55.5%.

2. Preparation of 2-methyl-9-dimethylthiocarbamoyloxy-4Hpyrido[1,2-a]pyrimidin-4-one XVI-1.

0.3 g of $K_2CO_3$ and 0.3 g of dimethylthiocarbamoyl chloride are added to a mixture of 0.3 g of the compound XV-1 provided in the said item (1) and 15 ml of acetone, and the resulting mixture is stirred at room temperature for 8 hours. The solid is filtered and washed with acetone. Then the washings are combined with the filtrate and concentrated. The residue is washed with water and dried over $P_2O_5$ to give 0.3 g of the titled compound XV-1.

Yield: 66.9%,
m.p.: 165°-167° C. (recrystallized from AcOEt),
Anal. Calcd. for $C_{12}H_{13}O_2N_3S$ C,54.79; H,4.88; N,15.94; S,12.07(%),
Found: C,54.74; H,4.98; N,15.96; S,12.18(%),
NMR ($CDCl_3$) δ: 2.37 (3H, s), 3.46 (6H, s).

3. Preparation of 2-methyl-9-dimethylcarbamoylthio-4H-pyrido[1,2-a]pyrimidin-4-one Ib-86

A suspension of 5.2 g of the compound XV-1 provided in the said item (2) in 40 ml of Dowtherm A (Dow Chemical Co.) is heated under reflux for 20 minutes. The reaction mixture is cooled and poured into 800 ml of n-hexane to give 5.0 g of the titled compound Ib-86.

m.p.: 165°-167° C. (recrystallized from AcOEt),
Anal. Calcd. for $C_{12}H_{13}O_2N_3S$ C,54.74; H,4.98; N,15.96; S,12.18(%),
Found: C,54.78; H,4.90; N,15.94; S,12.10(%),
NMR ($CDCl_3$) δ: 2.43 (3H, s), 3.10 (6H, s).

4. Preparation of 9-mercapto-2-methyl-4H-pyrido[1,2-a]pyrimidin-4-one II-3

A suspension of 0.4 g of NaH (60% oil disp.) in 20 ml of anhydrous THF is cooled at 0° C. 1.4 ml of n-propyl mercaptan is added dropwise to the reaction mixture, which is stirred for 20 minutes. 4.1 g of the compound Ib-86 provided in the said item (3) in 130 ml of anhydrous THF is added to the mixture. The reaction mixture is allowed to come to room temperature, and the mixture is stirred for 24 hours. The resulting mixture is concentrated in vacuo to dryness. The residue is dissolved in 100 ml of water, and mixed with 2 g of acetic acid. The crystal precipitated is filtered and dried to give 3.0 g of the titled compound II-3.

m.p.: 240°-241° C. (recrystallized from $CHCl_3$),
Anal. Calcd. for $C_9H_8ON_2S$ C,56.23; H,4.19; N,14.57; S,16.59,
Found: C,56.11; H,4.11; N,14.52; S,16.59.

PREPARATION

| | |
|---|---|
| 3-Ethoxycarbonyl-9-(4-methylphenylcarbamoylthio)-4H—pyrido-[1,2-a]pyrimidin-4-one Ia-1 | 25 mg |
| Lactose | 100 mg |
| Starch of wheat | 15 mg |
| Gelatin | 5 mg |

-continued

| | |
|---|---|
| Magnesium stearate | 5 mg |
| | 150 mg |

The components described above are charged to give a capsule.

EFFECT OF THE INVENTION

Experiment (Antiulcer activity to water-immersion stress ulcer)

SD male rats (body weight: 260-290 g) were fasted for 24 hours prior to the test. Rats were placed in a wire net cage for giving restraint stress and dipped in a water bath (23° C.) for 7 hours and killed. The stomach of each rat was removed and incised along the greater curvature. Length of each erosion in the glandular portion was measured and summed. Comparing the result of control group, inhibiting ratio againt the emergence of ulcer was calculated. Test compounds were suspended in 5% gum arabic solution and given orally 30 minutes before stressing.

Test compound

Cimetidine was used as a control drug.

Method of Indicates

Inhibition of ulcer formation above 71%, ++
Inhibition of ulcer formation from 51% to 70%, +

Result

Table 8 shows the result of the experiment.

TABLE 8

| Test Compound | Dose (mg/Kg) | Inhibition of ulcer |
|---|---|---|
| Ia-1 | 10 | ++ |
| | 3 | ++ |
| Ia-3 | 10 | ++ |
| Ia-4 | 10 | ++ |
| Ia-5 | 10 | + |
| Ia-7 | 10 | ++ |
| Ia-8 | 10 | ++ |
| Id-22 | 10 | ++ |
| Ie-28 | 10 | ++ |
| Ie-29 | 10 | + |
| Ie-33 | 10 | ++ |
| Ie-34 | 10 | + |
| Ie-37 | 10 | ++ |
| Ie-42 | 10 | ++ |
| Ie-46 | 10 | ++ |

TABLE 8-continued

| Test Compound | Dose (mg/Kg) | Inhibition of ulcer |
|---|---|---|
| Ie-56 | 3 | + |
| Ie-57 | 10 | ++ |
| Ie-63 | 10 | ++ |
| Ie-66 | 3 | ++ |
| Ie-67 | 10 | ++ |
| Ie-71 | 10 | + |
| Ie-74 | 10 | ++ |
| Ie-77 | 10 | ++ |
| cimetidine | 100 | ++ |

The result of the above experiment show that the compounds (I) of the present invention have potent antiulcer activity. Thus the compond (I) are effective for prophylactic and therapeutic of ulcer or for inhibition of ulcer recurrence after withdrawal of drugs.

What is claimed is:

1. A compound of the formula:

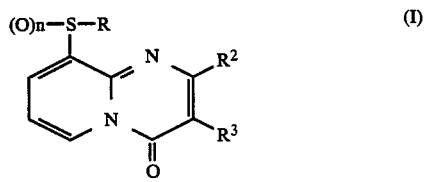

wherein
n is 0 or 1,
R is $-COR^1$,
$R^1$ is isoxazolyl, oxazolyl or thiazolyl, and
$R^2$ and $R^3$ are each hydrogen, $C_1$-$C_5$ alkyl, carboxy, $C_2$-$C_5$ alkoxycarbonyl or benzyloxycarbonyl, optionally substituted by one or two members selected from the group consisting of $C_1$-$C_3$ alkyl, $C_1$-$C_3$ alkoxy and halogen.

2. The compound according to claim 1, wherein $R^1$ is isoxazolyl.

3. The compound according to claim 1, wherein $R^1$ is oxazolyl.

4. The compound according to claim 1, wherein $R^1$ is thiazolyl.

5. The compound according to claim 1, wherein $R^2$ and $R^3$ are each hydrogen, $C_1$-$C_3$ alkyl, carboxy or $C_2$-$C_5$ alkoxycarbonyl.

6. A pharmaceutical composition for treating a patient suffering from peptic ulcer comprising a pharmacologically effective amount of a compound according to claim 1 and a pharmaceutically acceptable carrier, diluent or excipient.

* * * * *